United States Patent
Matsunami

(10) Patent No.: US 12,127,927 B2
(45) Date of Patent: Oct. 29, 2024

(54) MEDICAL TOOL

(71) Applicant: SOSAIKOUSEIKAI CLINICAL FOUNDATION MATSUNAMI RESEARCH PARK, Gifu-ken (JP)

(72) Inventor: Hidetoshi Matsunami, Gifu-ken (JP)

(73) Assignee: SOSAIKOUSEIKAI CLINICAL FOUNDATION MATSUNAMI RESEARCH PARK, Gifu-ken (JP)

(*) Notice: Subject to any disclaimer, the term of this patent is extended or adjusted under 35 U.S.C. 154(b) by 869 days.

(21) Appl. No.: 17/285,467

(22) PCT Filed: Oct. 16, 2019

(86) PCT No.: PCT/JP2019/040546
§ 371 (c)(1),
(2) Date: Apr. 14, 2021

(87) PCT Pub. No.: WO2020/080379
PCT Pub. Date: Apr. 23, 2020

(65) Prior Publication Data
US 2021/0378812 A1   Dec. 9, 2021

(30) Foreign Application Priority Data
Oct. 19, 2018 (JP) ................. 2018-197272

(51) Int. Cl.
*A61F 2/04* (2013.01)
*A61F 5/00* (2006.01)
*A61M 27/00* (2006.01)

(52) U.S. Cl.
CPC .............. *A61F 2/04* (2013.01); *A61F 5/0076* (2013.01); *A61M 27/002* (2013.01);
(Continued)

(58) Field of Classification Search
CPC .... A61F 2/04; A61F 5/0076; A61F 2002/045; A61F 2210/0019; A61F 2220/0016; A61M 27/00; A61M 2210/1053
(Continued)

(56) References Cited

U.S. PATENT DOCUMENTS

| | | | |
|---|---|---|---|
| 2008/0058840 A1* | 3/2008 | Albrecht | ............... A61F 5/0036 606/153 |
| 2008/0255678 A1* | 10/2008 | Cully | ........................ A61F 2/04 623/23.65 |

(Continued)

FOREIGN PATENT DOCUMENTS

| | | | |
|---|---|---|---|
| CN | 102083393 A | 6/2011 | |
| JP | 2007513685 A | 5/2007 | |

(Continued)

OTHER PUBLICATIONS

Second Office Action of the China National Intellectual Property Administration (CNIPA) dated May 8, 2024, in related Chinese Appl. No. 201980067828.X, 14 pages.

(Continued)

*Primary Examiner* — Andrew J Mensh
(74) *Attorney, Agent, or Firm* — Bochner PLLC; Andrew D. Bochner

(57) ABSTRACT

A medical tool for placement in a digestive tract lumen includes a tubular portion, which opens at two ends, and an annular attachment portion, which is configured to be fixed to at least a part of the tubular portion and be capable of installing the tubular portion in the digestive tract lumen. The tubular portion is placeable along the digestive tract, has a side surface that is capable of conforming to the shape of the inner wall of the digestive tract, and allows digestive (Continued)

juice or digested contents to permeate. The attachment portion is configured to be placeable in the stomach through the mouth.

4 Claims, 22 Drawing Sheets

(52) U.S. Cl.
CPC . *A61F 2002/045* (2013.01); *A61F 2210/0019* (2013.01); *A61F 2220/0016* (2013.01); *A61M 2210/1053* (2013.01)

(58) Field of Classification Search
USPC .............................................. 604/8
See application file for complete search history.

(56) References Cited

U.S. PATENT DOCUMENTS

| | | | | |
|---|---|---|---|---|
| 2010/0298929 | A1* | 11/2010 | Thornton | A61F 2/246 623/2.1 |
| 2012/0116285 | A1* | 5/2012 | Duggirala | A61F 5/0079 604/8 |
| 2013/0030350 | A1* | 1/2013 | Albrecht | A61F 5/0036 604/8 |
| 2013/0289718 | A1 | 10/2013 | Tsukashima et al. | |
| 2014/0142719 | A1* | 5/2014 | Gittard | A61F 2/958 623/23.65 |
| 2014/0378884 | A1* | 12/2014 | Provenza | A61F 5/003 604/8 |
| 2017/0135835 | A1* | 5/2017 | Matsunami | A61F 5/0076 |
| 2017/0312111 | A1* | 11/2017 | Sharma | A61F 5/003 |

FOREIGN PATENT DOCUMENTS

| | | |
|---|---|---|
| JP | 2010-502312 A | 1/2010 |
| WO | WO2005060869 A1 | 7/2005 |
| WO | 2009126294 A1 | 10/2009 |
| WO | WO2013026473 A1 | 2/2013 |
| WO | WO2015146612 A1 | 10/2015 |

OTHER PUBLICATIONS

International Search Report for International Application No. PCT/JP2019/040546, dated Nov. 26, 2019, 2 pages.

* cited by examiner

Fig.26A
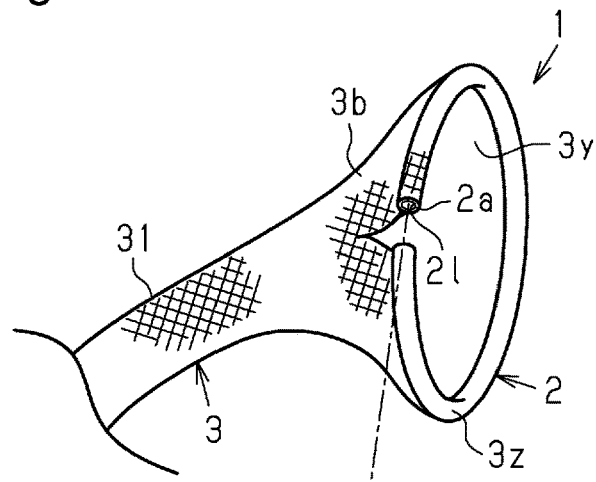
Fig.26D
Fig.26C
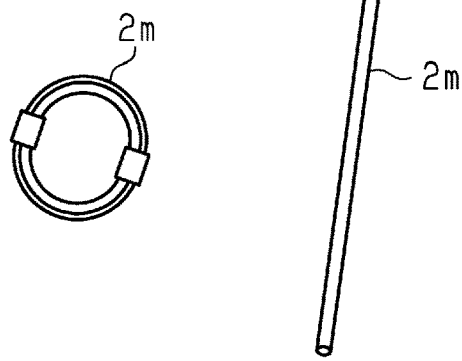
Fig.26B
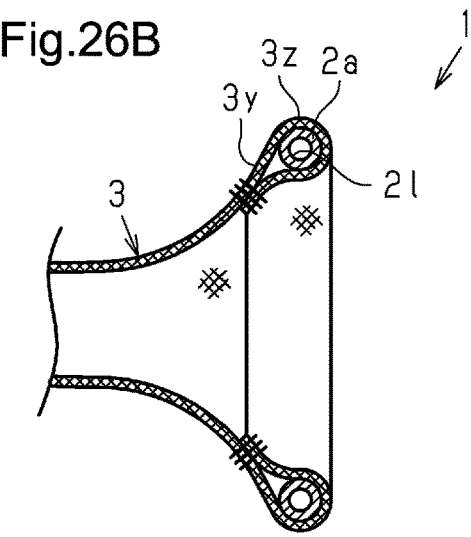
Fig.26E
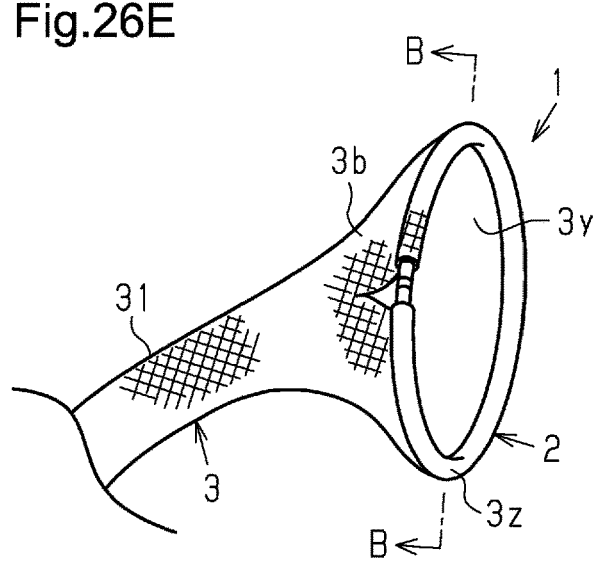

Fig.28A
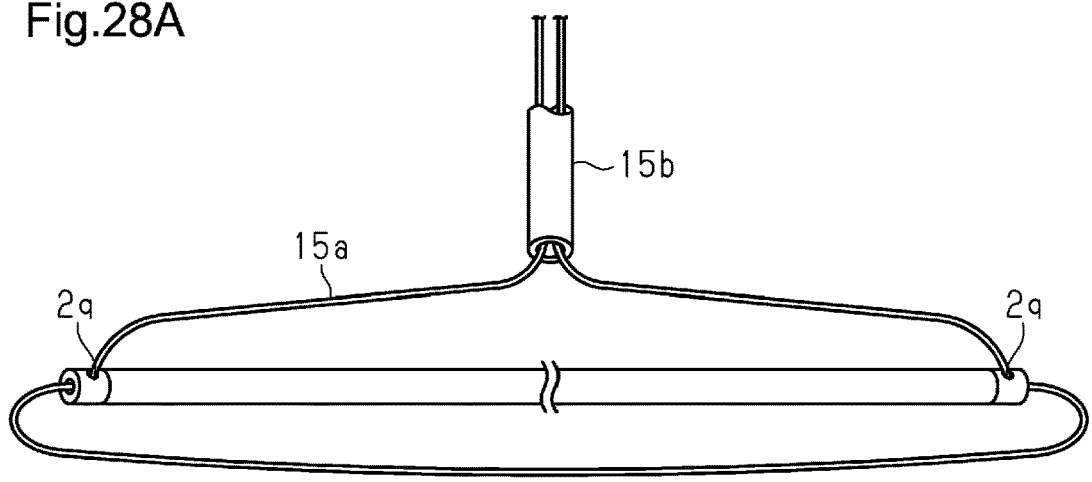
Fig.28F
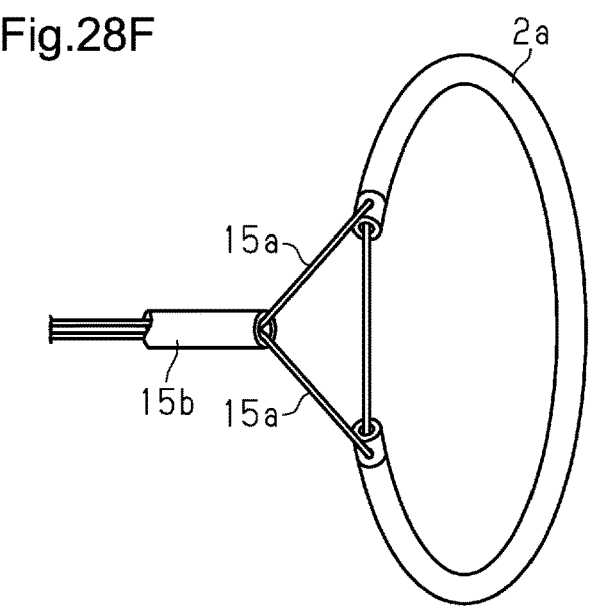
Fig.28C  Fig.28D
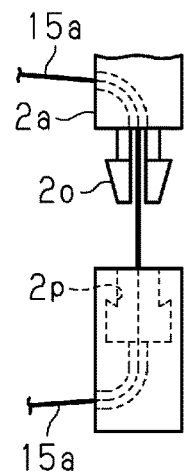 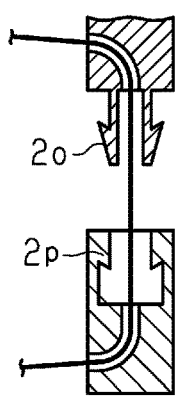
Fig.28B
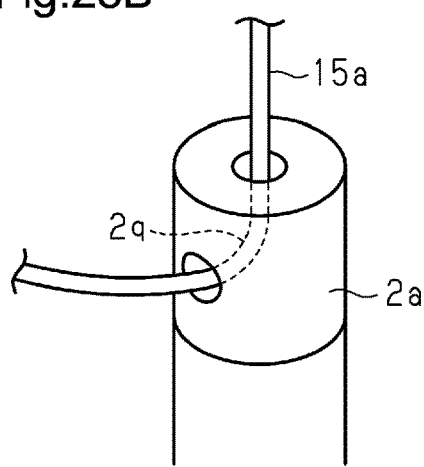
Fig.28E
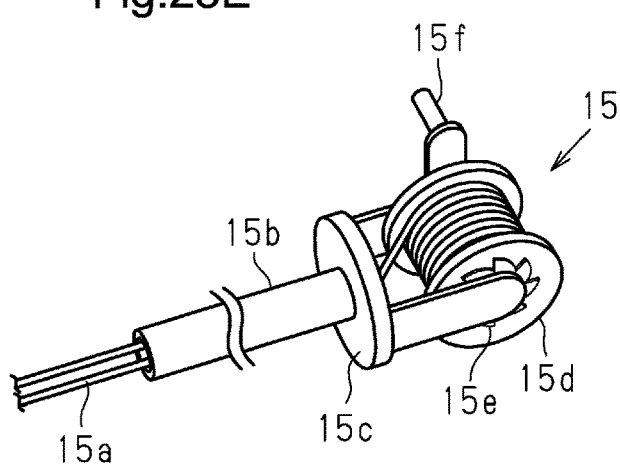

MEDICAL TOOL

TECHNICAL FIELD

The present invention relates to a medical tool, and more particularly to a medical tool for placement in a digestive tract lumen.

BACKGROUND ART

A medical tool for treating obesity is known that includes a sleeve and an anchor and is placed in the gastrointestinal tract lumen. This medical tool limits digestion and absorption by blocking the contact between food and the gastrointestinal mucosa (Patent Document 1).

However, when this medical tool inhibits gastrointestinal motility, such as peristaltic movements, and blocks the contact between the food and the gastrointestinal mucosa, the gastrointestinal mucosa may become and remain atrophied. Furthermore, when the hard medical tool continuously presses the inner wall of the digestive tract, the mucosa of the pressed region is at risk for compression necrosis.

In response to the above issues, the present inventor has developed a medical tool capable of preventing atrophy of the gastrointestinal mucosa while limiting digestion and absorption. Patent Document 2 describes this medical tool.

This invention relates to a medical tool for placement in a digestive tract lumen. The medical tool includes at least one tubular portion, which has at least one open end, and at least one attachment portion, which is provided in at least a part of the tubular portion and configured to be capable of installing the medical tool in the digestive tract lumen. The tubular portion is configured to be placeable along at least a part of the digestive tract and has a side surface at least a part of which is capable of conforming to the shape of the inner wall of the digestive tract.

The medical tool may have any suitable configuration that can be installed in the digestive tract lumen via the attachment portion.

The attachment portion may have any configuration as long as it can fix the medical tool in the digestive tract lumen. For example, the attachment portion may be capable of attaching the medical tool in the digestive tract lumen via another member, or may be capable of directly attaching the medical tool in the digestive tract lumen, such as to the stomach wall.

The attachment portion may have any suitable configuration that is attachable in the digestive tract lumen via another member. Examples of this another attachment member include a suture for suturation.

Examples of the configuration that can directly attach the attachment portion in the digestive tract lumen include a stent placed in the duodenum.

PRIOR ART DOCUMENTS

Patent Documents

Patent Document 1: Japanese Laid-Open Patent Publication No. 2007-513685
Patent Document 2: Japanese Patent Re-Publication No. WO2015/146612

SUMMARY OF THE INVENTION

Problems that the Invention is to Solve

In the invention described in Patent Document 1, the tool is fixed by a stent or a corrugated anchor in the duodenum, eliminating the need for laparotomy. However, since the device is attached so as to be pressed against the inner wall of the duodenum, which is a section of the digestive tract lumen that has a small inner diameter, the tool tends to damage the mucosa of the duodenum.

The invention of Patent Document 2 involves gastrostomy to form a stomach incision part in the front side of the stomach and surgery to form an intestinal perforation part in the intestinal tract. A blunt needle with a thread is inserted through the intestinal perforation part and taken out through the stomach incision part. The tubular portion of the medical tool is tied to the blunt needle with a thread, which is then returned into the intestinal tract to place the tubular portion in the intestinal tract and thus place the attachment portion in the pyloric region. Through the stomach incision part, the attachment portion may be fixed and stabilized in the digestive tract lumen by suturing with a suture, for example. That is, this invention disadvantageously requires laparotomy to place the ring-shaped anchor.

An objective to be solved by the present invention is to provide a medical tool that can be stably placed with minimal burden on the subject.

Means for Solving the Problems

To achieve the foregoing objective, a medical tool for placement in a digestive tract lumen of the present invention includes at least one tubular portion opening at two ends, and at least one attachment portion configured to be fixed to at least a part of the tubular portion and be capable of installing the tubular portion in the digestive tract lumen. The tubular portion is configured to be placeable along at least a part of a digestive tract, include a side surface, at least a part of which is capable of conforming to a shape of an inner wall of the digestive tract, and allow a part of digestive juice or digested contents to permeate. The attachment portion is configured to be placeable in a stomach through a mouth.

The present invention places the attachment portion in the stomach through the oral cavity and with an endoscope or the like. This provides an advantageous effect that a medical tool that can alleviate serious obesity is usable without the need for laparotomy or the like, reducing the burden on the subject.

Unlike bypass surgery, the medical tool can be removed reversibly, allowing for the appropriate selection between use and disuse according to the subject.

The present invention may also allow the attachment portion to be fixed to the stomach wall by any of a suture, a stapler, a clip, a hook, or an adhesive to be stably positioned.

The attachment portion can be placed in the pyloric region of the stomach and be sized so as not to pass through the pylorus after placement. This configuration allows the attachment portion to function as an anchor and remain in the stomach, enabling the tubular portion to extend from the duodenum to the jejunum.

The attachment portion may be made of a medical metal. In particular, the attachment portion may be made of a shape memory alloy, assume the memorized shape at body temperature or higher, and change its shape at a temperature lower than body temperature. This attachment portion may be made of a Ni—Ti alloy, for example.

The attachment portion may preferably be plated or plastic coated.

The attachment portion may also be made of plastic, ceramic, or fiber.

Also, a medical tool for placement in a digestive tract lumen of the present invention includes at least one tubular portion opening at two ends, and at least one attachment portion that is configured to attach the tubular portion to the digestive tract lumen. The tubular portion is configured to be placeable along at least a part of a digestive tract, include a side surface at least a part of which is capable of conforming to a shape of an inner wall of the digestive tract, and allow a part of digestive juice or digested contents to permeate. The attachment portion is configured to be placeable in the stomach through a mouth, and assume an annular shape.

Since the attachment portion is annular and surrounds the pylorus, the attachment portion is stably placed in the stomach and thus allows the contents to smoothly move to the duodenum through the annular opening.

The attachment portion may have the shape of a donut-shaped disc or the side surface of a truncated cone, and may be collapsed before the placement and deployed during the placement. Also, the attachment portion may have the shape of a funnel or a trumpet or may have a mesh configuration. These shapes allow the attachment portion to be placed more stably.

The attachment portion may include a hollow donut-shaped bag and a filler to be introduced into the bag, and the filler may be introduced into the bag after the attachment portion is inserted into the stomach.

Furthermore, the attachment portion may be made of a flexible material and cured by a curing means during the placement. For example, the flexible material may include an ultraviolet curable resin, and the curing means may be an ultraviolet irradiation device.

The attachment portion may include a plurality of members and a string-shaped member extending through these members. The string-shaped member may be tightened to integrate the members into an annular shape.

The attachment portion may include a deformable tube of bellows or a flexible pipe and be configured to assume an annular shape during the placement.

The attachment portion may include a wire-shaped member having a bendable bending section and an engageable engaging section in parts of the wire-shaped member, and the attachment portion may be configured to assume an annular shape during the placement.

The attachment portion may be a linear member formed by an elastic member, include connecting sections at two ends of the attachment portion, and be configured to assume an annular shape when the connecting sections are engaged during the placement. In this case, the connecting sections may preferably be structures that are magnetically attracted and attached.

The attachment portion may be configured so that one end of the tubular portion is folded back and fixed to surround the attachment portion.

The attachment portion may also include a cutting section that is made of a material having a lower melting point than other sections and is melted when endoscopically heated with a heater. The cutting section may be a section that has a smaller diameter or is made of a material with low strength so that this section is easily cut with scissors and an endoscope.

The attachment portion may be made of a material that is degradable in the digestive tract lumen, such as a biodegradable material.

The tubular portion and the whole or a part of the attachment portion may be separately delivered into the stomach through the mouth and then combined together in the stomach as the medical tool.

Effects of the Invention

The present invention provides a medical tool that is easily placed in the stomach through the mouth, thereby minimizing the burden on the subject, and allows the attachment member to be stably placed in the stomach.

BRIEF DESCRIPTION OF THE DRAWINGS

FIG. 19C is a schematic view showing a collapsed shape of a modification of the attachment member of the example of FIG. 19A.

FIG. 26A is a perspective view of a tubular portion of an example in which the tubular portion is separate from the attachment member.

FIG. 26B is an end view of the tubular portion of the example of FIG. 26A.

FIG. 26C is a perspective view of the core member that is wound and bound in the example of FIG. 26A.

FIG. 26D is a perspective view of the core member in an extended state of the example of FIG. 26A.

FIG. 26E is a perspective view in which the core member is attached to the tubular portion of the example of FIG. 26A.

FIG. 28A is a perspective view of a state in which an attachment member is attached to a wire winder in an example in which the tubular portion is separate from the attachment member.

FIG. 28B is a partial perspective view showing a wire passage of an attachment portion of the example of FIG. 28A.

FIG. 28C is a perspective view showing an insertion portion and a fitting portion of the attachment member of the example of FIG. 28A.

FIG. 28D is a cross-sectional view showing the insertion portion and the fitting portion of the attachment member of the example of FIG. 28A.

FIG. 28E is a perspective view showing the wire winder of the example of FIG. 28A.

MODES FOR CARRYING OUT THE INVENTION

Embodiments of the present invention are described below with reference to the drawings, but the present invention is not limited to these embodiments.

<A-1. Overall Configuration of Medical Tool>

Figure 1:
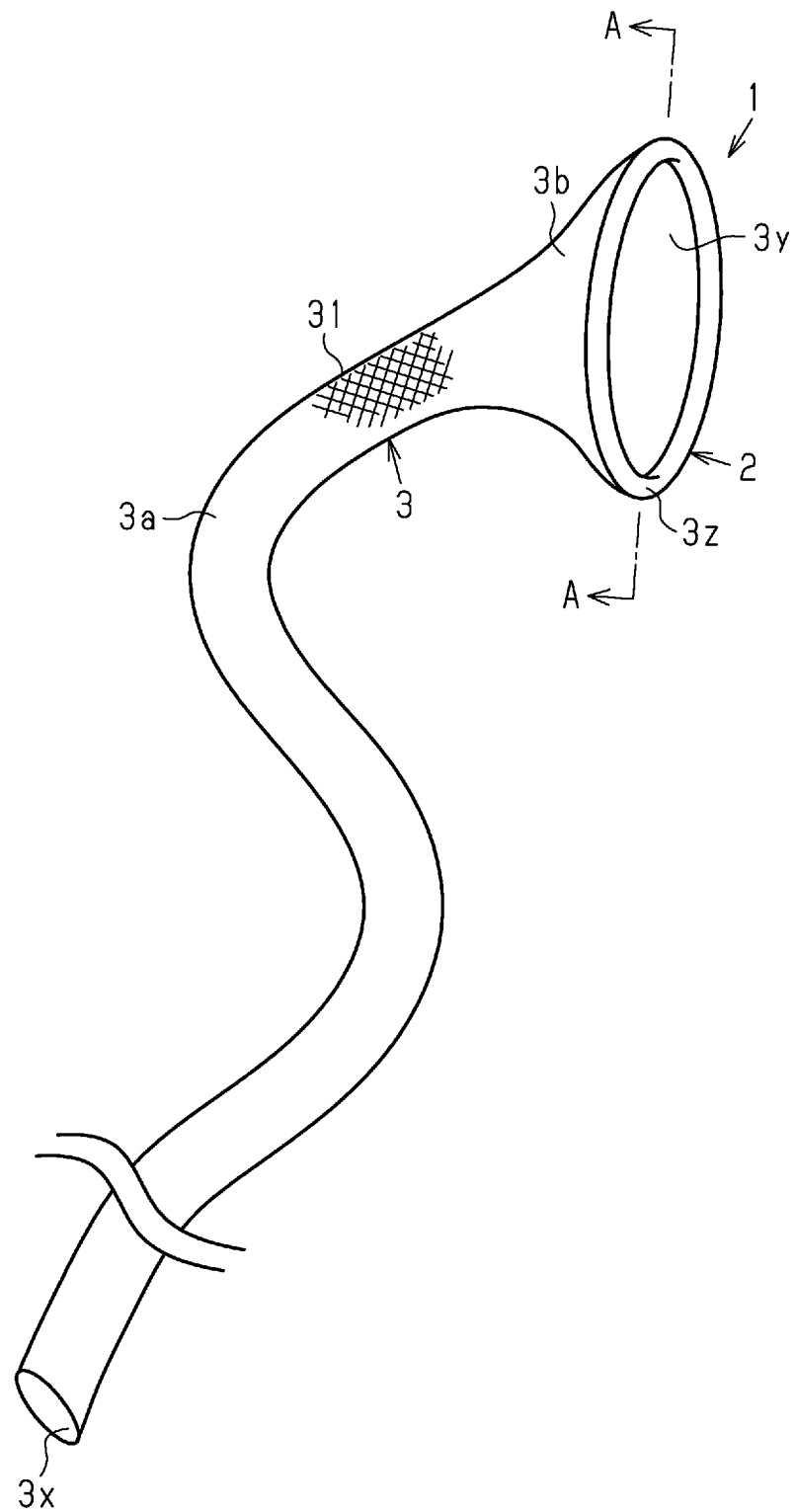
FIG. 1 is a schematic view of a medical tool according to one embodiment of the present invention.

FIG. 1 is a schematic view of a medical tool 1 according to one embodiment of the present invention.

<Medical Tool 1>

As shown in FIG. 1, the medical tool 1 of the present embodiment includes one attachment portion 2 and one tubular portion 3.

The tubular portion 3 of the present embodiment opens at least at an end. In embodiments, the tubular portion 3 opens at two ends (that is, an end section 3x opposite to the attachment portion 2 and an end section 3y at the attachment portion 2).

<Attachment Portion 2>

The attachment portion 2 is fixed at least to an arbitrary part of the tubular portion 3 to hold the position of the tubular portion 3. In embodiments, the attachment portion 2 is provided at the end section 3y of the tubular portion 3.

The attachment portion 2 and the tubular portion 3 may be integrally formed, or may be separate members connected to each other. In embodiments, the attachment portion 2 and the tubular portion 3 appear to be integrally formed.

Figure 2:
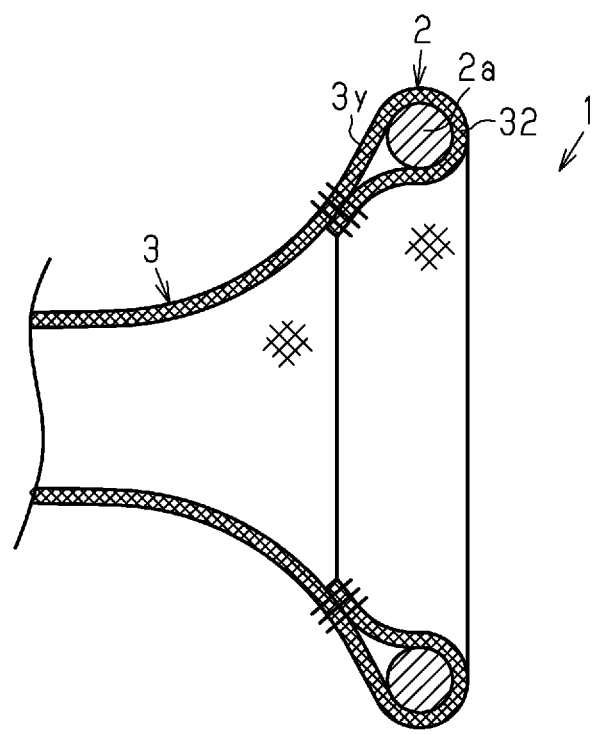
FIG. 2 is a cross-sectional view of an attachment portion of the medical tool of FIG. 1.

FIG. 2 is a cross-sectional view of the configuration of the attachment portion 2 taken along line A-A in FIG. 1A. As shown in FIG. 2, the attachment portion 2 has an annular attachment member 2a, and the end section 3y of the tubular portion 3 encloses the attachment member 2a from the outside. The end section 3y of the tubular portion 3 is folded back over the inner side of the annular attachment member 2a. The folded end section 3y is placed over and fixed to the section of the tubular portion 3 located on the outer side. Here, the end section 3y is fixed by suturing to form a fixing portion 3z (see FIG. 1). The end section of the medical tool 1 configured in this manner serves as the attachment portion 2.

The shape of the attachment portion 2 is not necessarily limited to an annular shape. The attachment portion 2 may have any shape that can install the medical tool 1 in an appropriate position in the digestive tract lumen. In the medical tool 1, the attachment portion 2 may be formed integrally, fixed to the tubular portion 3 to form a single unit, or attached to the medical tool 1 via a different member when the medical tool 1 is installed in the digestive tract lumen.

<Placement of Medical Tool 1>

Figure 3:
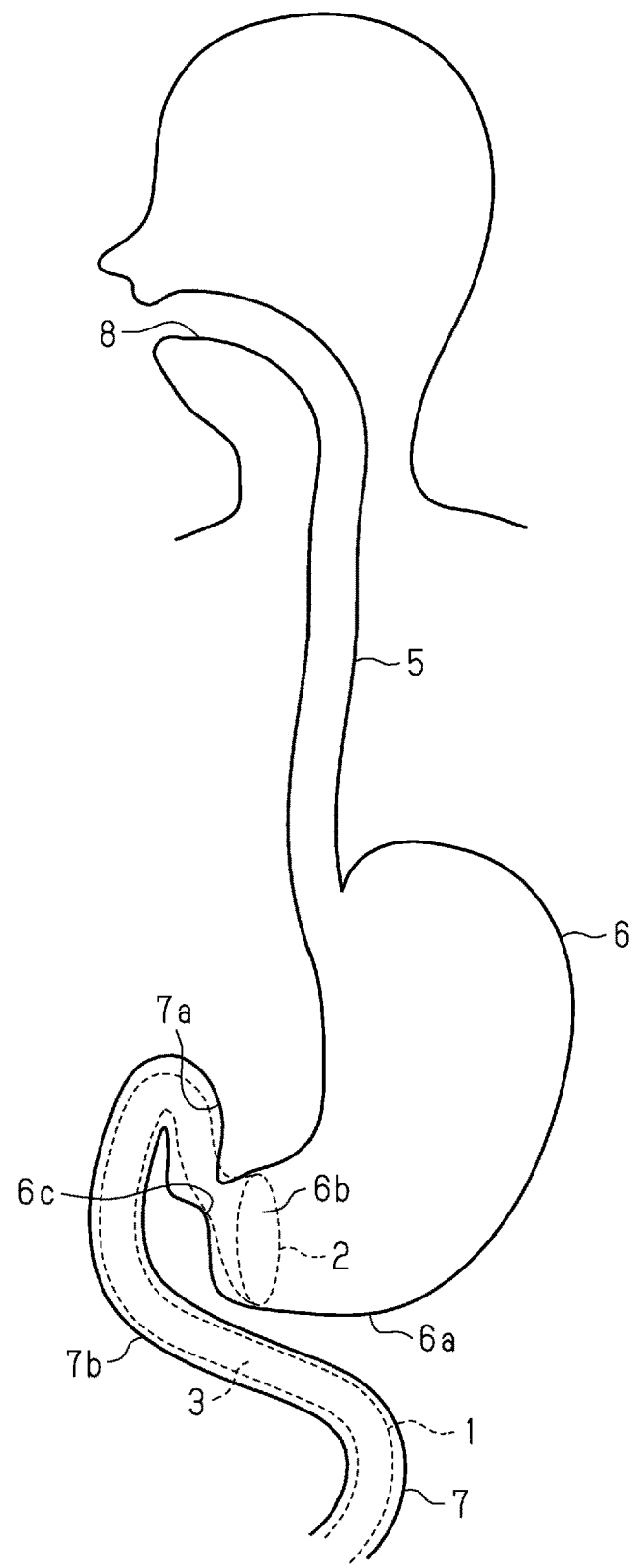
FIG. 3 is a schematic view showing the placement of the medical tool of FIG. 1 in a digestive tract.
Figure 4:
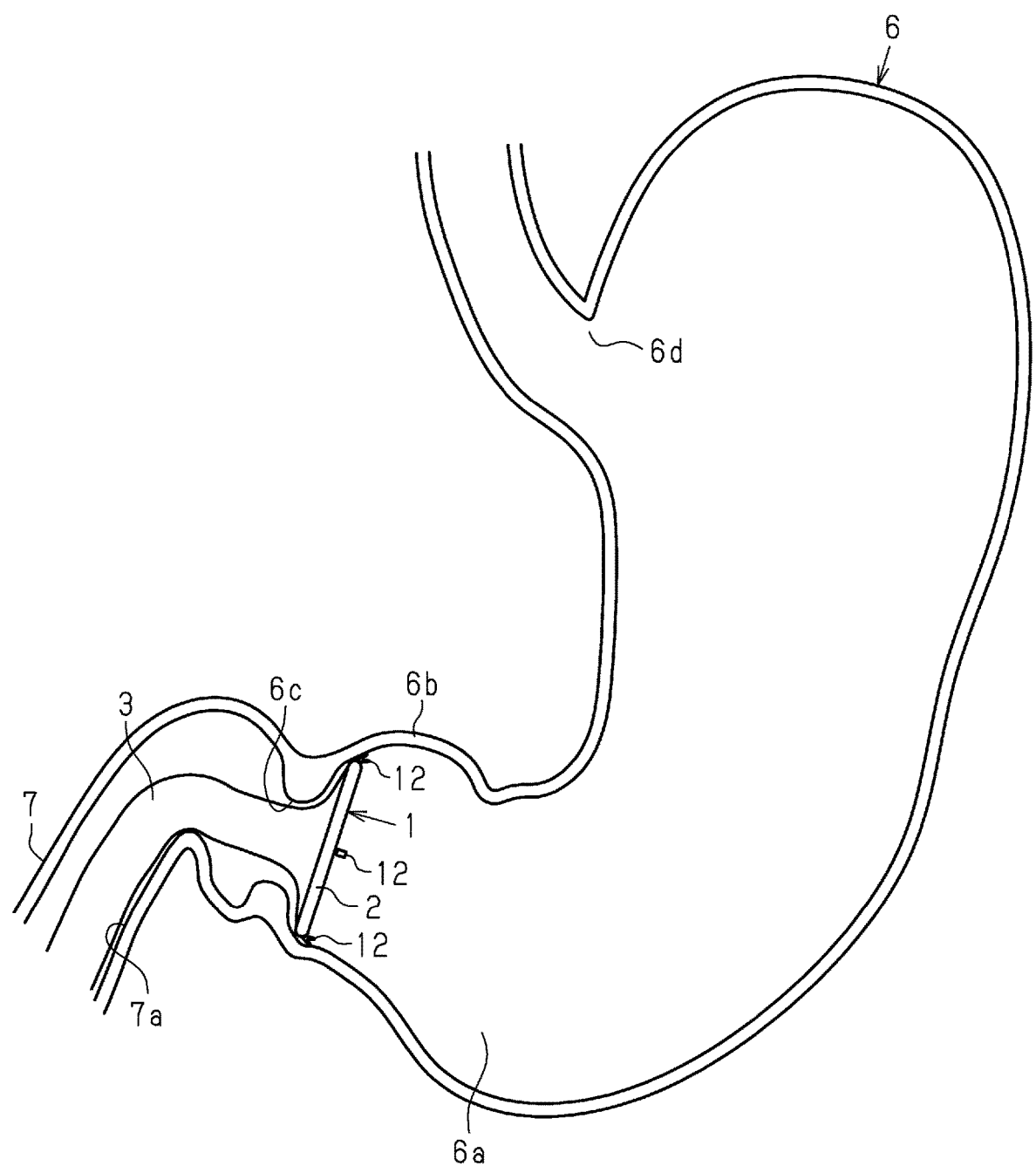
FIG. 4 is a schematic view showing the attachment portion placed in the pyloric region of a stomach.

FIG. 3 is a schematic view showing the placement of the medical tool 1 in the digestive tract. FIG. 4 is a schematic view showing the attachment portion 2 placed at the pyloric antrum 6b in the pyloric region 6a of the stomach 6. The medical tool 1 is placed in the digestive tract from the stomach 6 to the intestinal tract 7. In this case, when the attachment portion 2 has a diameter that is sized so that the attachment portion 2 cannot normally pass through the pylorus 6c, the attachment portion 2 does not have to be fixed with clips 12, 14 (see FIGS. 23 and 24) as shown in FIG. 4, for example.

As shown in FIG. 4, the attachment portion 2 of the medical tool 1 is placed at the pyloric antrum 6b in the pyloric region 6a. The attachment portion 2 is generally annular and has a diameter that is sized so that the attachment portion 2 cannot normally pass through the pylorus 6c. The attachment portion 2 is thus retained in the pyloric antrum 6b without being fixed to the stomach wall. Nevertheless, the position of the attachment portion 2 may be fixed and stabilized with clips 12, for example.

In any case, to orally place the medical tool 1, the attachment portion 2 needs to pass through the cardia 6d.

As shown in FIG. 3, the tubular portion 3, which is continuous with the attachment portion 2, is flexible and thus extends through the pylorus 6c into the duodenum 7a and then further into the jejunum 7b due to the peristaltic movement of the digestive tract. As a result, the tubular portion 3 extends from the duodenum 7a along the inner wall of the jejunum 7b.

<Deformation of Attachment Portion 2 for Oral Placement>

The attachment portion 2 of the present embodiment is characterized in that it can be placed orally, that is, it can be introduced non-invasively into the stomach 6 from the oral cavity 8 through the esophagus 5 as shown in FIG. 3. The attachment portion 2 fixes the tubular portion 3 extending from the stomach 6 to the intestinal tract 7. The present embodiment does not necessarily exclude the placement into the digestive tract lumen that is achieved by an invasive method such as laparotomy. However, the main technical feature is that the attachment portion 2 can be easily placed in the digestive tract lumen through the mouth and the esophagus 5 principally in a minimally invasive or non-invasive manner.

The present embodiment is also characterized in that, in principle, the attachment portion 2 has a predetermined size and is thus configured so as not to pass through the pylorus 6c after orally placed, allowing the medical tool 1 to be retained in the digestive tract lumen without being directly fixed to the inner wall of the stomach 6.

In another example, the attachment portion 2 is smaller than the inner diameter of the pylorus 6c. In this case, a fixing means may be used to stabilize the position of the medical tool 1 by minimally invasive technique.

In the present embodiment, to orally place and retain the medical tool 1 within the stomach 6, the outer dimension of the medical tool 1 during oral placement needs to be smaller than the inner diameter of the esophagus 5 so as to pass through the esophagus 5. Additionally, the outer dimension needs to be larger than the inner diameter of the pylorus 6c to retain the medical tool 1 in the cavity of the stomach 6. In another embodiment in which the attachment portion 2 is fixed to the stomach wall 6e with a fixing means such as clips 12 and 14, the attachment portion 2 may be smaller than the inner diameter of the pylorus 6c.

The attachment portion 2 needs to be configured so as not to pass through the pylorus 6c and also needs to allow the smooth movement of food or the like from the stomach 6 into the tubular portion 3 placed in the intestinal tract 7. As such, it is generally preferable that its deployed shape be, but not limited to, an annular shape in order to open the tubular portion 3 and stably hold it near the pylorus 6c.

To meet the objective of the safe passage through the oral cavity 8 and the esophagus 5, the attachment portion 2 may be made of a material having flexibility that can be changed under certain conditions, for example. Alternatively, the attachment portion 2 may be physically configured such that it is disassembled or collapsed for insertion and then assembled or expanded for deployment. In another conceivable configuration, a flexible composition or a fluid is coagulated and cured in the gastric cavity.

To stably hold the attachment portion 2 in the cavity of the stomach 6, particularly at the pyloric antrum 6b, it preferably has the shape of an annular ring, a donut-shaped disc, or the like. Other preferable shapes include the shape of the side surface of a truncated cone and the shape of a funnel with its opening stably positioned at the pylorus 6c so that the contents in the gastric cavity can be smoothly introduced into the tubular portion 3.

In another preferable example, the attachment portion 2 is bent and collapsed into a narrow shape to increase its stability.

To this end, the attachment portion 2 may have any suitable shape that allows the attachment in the digestive tract lumen via another member. The configurations described above increase the stability of the medical tool 1 when fixed.

Details will be given in the descriptions of examples, but any configuration may be used that provides the required strength for the required period according to the purpose.

In an example of a minimally invasive procedure for placing the medical tool 1 in a more stable position, the medical tool 1 may be fixed endoscopically with clips 12 or 14 (see FIGS. 23 and 24) as will be described below. Also, threads (e.g., sutures), staplers, hooks, and adhesives, or combinations thereof may be used for the fixation to the body wall. Alternatively, the position of the attachment portion 2 is fixed by the tubular portion 3 being pulled by the peristaltic movement, without requiring the fixing means described above.

To eliminate or remove the medical tool 1, the attachment portion 2, which retains and fixes the medical tool 1, may be deformed or disassembled. To this end, it is further preferable that the attachment portion 2 be configured so that the whole or a part of it can be cut, dissolved, or softened, for example. Alternatively, the attachment portion 2 may be made of a material that degrades over time in the digestive tract lumen so that it does not need to be taken out.

The individual configurations of modifications will be described below in detail.

<Tubular Portion 3>

The tubular portion 3 is configured to be placeable along at least a part of the digestive tract. The tubular portion 3 can easily deform. Since its cross-sectional area and shape are changeable, at least a part of the side surface of the tubular portion 3 is capable of conforming to the shape of the inner wall of the digestive tract. As used herein, the configuration that is capable of conforming to the shape of the inner wall of the digestive tract refers to a configuration that can be brought into and out of close contact with the inner wall of the digestive tract according to the gastrointestinal motility when the medical tool 1 is used.

The tubular portion 3 may have any longitudinal length suitable to achieve the intended effect. The length may be, but not limited to, 30 cm to 9 m, for example.

The length of the tubular portion 3 is set by taking into account the ease of placement of the medical tool 1 in the digestive tract lumen, in addition to the effect of limiting digestion and absorption. Unless otherwise specified, the shape, area, and length of each member as defined herein refer to the shape, area, and length of the member of the medical tool 1 in the initial state.

In use of the medical tool 1, the tubular portion 3 may be expandable or non-expandable in the longitudinal direction. Preferably, the tubular portion 3 is non-expandable in the longitudinal direction. When the tubular portion 3 is non-expandable in the longitudinal direction, the position of the end section 3x of the tubular portion 3 is stable when the medical tool 1 is used. As used herein, the term "non-expandable" refers, for example, to a state in which the length at maximum expansion is approximately 110% or less of the length before expansion.

At least a part of the tubular portion 3 is typically deformable in response to gastrointestinal motility. This configuration improves the conformability of the tubular portion to the shape of the inner wall of the digestive tract and maintains the physical stimuli given to the inner wall of the digestive tract by the digested contents. This improves the effect of preventing gastrointestinal mucosal atrophy.

At least a part of the tubular portion 3 is typically expandable in the radial direction of the tubular portion 3 in response to gastrointestinal motility. The proportion of the cross-sectional area at maximum expansion of a cross-section of at least a part of the tubular portion 3 to the normal cross-sectional area of this cross-section may be any suitable proportion. In one example, the proportion may be greater than or equal to 200%. The configuration ensures that the tubular portion conforms to the shape of the inner wall of the digestive tract when the digested contents pass through the digestive tract and expand the digestive tract in the cross-sectional direction. This improves the effect of preventing gastrointestinal mucosal atrophy. In another example, the proportion may be less than or equal to 10,000%.

At least a part of the tubular portion 3 is typically contractible in the radial direction of the tubular portion 3 in response to gastrointestinal motility. The proportion of the cross-sectional area at maximum contraction of a cross-section of at least a part of the tubular portion 3 to the normal cross-sectional area of this cross-section may be any suitable proportion. In one example, the proportion may be less than or equal to 75%. The above configuration further ensures that the tubular portion conforms to the shape of the inner wall of the digestive tract when the digestive tract contracts in the cross-sectional direction due to gastrointestinal motility. This improves the effect of preventing gastrointestinal mucosal atrophy. In another example, the proportion may be greater than or equal to 0.5%.

The tubular portion 3 may have any suitable cross-sectional shape. Examples of this shape include a circular shape.

In the example shown in FIG. 1, the tubular portion 3 has a uniform region 3a, in which the cross-sectional area of the tubular portion 3 is substantially uniform, and an increasing region 3b, in which the cross-sectional area of the tubular portion 3 increases. The uniform region 3a extends in the direction from the end section 3x toward the end section 3y. The increasing region 3b extends from the end section 3y to the end of the uniform region 3a closer to the end section 3y. The increasing region 3b is tapered such that the cross-sectional area of the tubular portion 3 increases toward the end section 3y. The uniform region 3a allows the tubular portion 3 to be easily placed along at least a part of the digestive tract. Since the tubular portion 3 has the increasing region 3b, the medical tool 1 can be more stably placed in the digestive tract lumen.

The length of the uniform region 3a may be 60% or more, preferably 80% or more, of the length of the entire tubular portion 3.

The uniform region 3a may have any suitable cross-sectional area. In one example, the cross-sectional area is 2 $cm^2$ to 12 $cm^2$. The above configuration improves the effect of preventing gastrointestinal mucosal atrophy, and allows the tubular portion to be more easily placed along at least a part of the digestive tract lumen.

The tubular portion 3 is typically configured to allow a part of digestive juices and digested contents to permeate. In this configuration, the digestive juice and digested contents do not completely bypass the original path when the medical tool 1 is used. This avoids the rapid passage of food into the lower section of the small intestine. As a result, the dumping syndrome, which can occur in the subject after eating, can be effectively prevented. The dumping syndrome is a condition that occurs in the subject when the food does not stay in the stomach after eating and rapidly moves into the lower section of the small intestine, causing symptoms such as nausea, vomiting, lassitude, palpitation, and sweating. Since these unpleasant symptoms that would otherwise occur in the subject are reduced, obesity can be treated more comfortably. Furthermore, the use of the medical tool 1 provides a more physiological state.

The tubular portion 3 can have any suitable shape. At least a part of the tubular portion 3 may be net-shaped, strip-shaped, slit-shaped, perforated, unevenly shaped, membrane-shaped, randomly shaped like non-woven fabric, or a combination thereof, for example. Preferably, at least a part of the tubular portion 3 has openings and is net-shaped, strip-shaped, slit-shaped, perforated, or a combination thereof. More preferably, at least a part of the tubular portion 3 is net-shaped. The present specification focuses on a net 31 of an embodiment shown in FIG. 1 (an embodiment in which the entire tubular portion 3 is net-shaped), and the descriptions on other embodiments are omitted.

When at least a part of the tubular portion 3 is net-shaped, strip-shaped, slit-shaped, perforated, or a combination thereof, the tubular portion can easily deform and thus has higher conformability to the shape of the inner wall of the digestive tract. This more effectively limits the reduction in gastrointestinal motility and further increases the physical stimuli to the inner wall of the digestive tract. The effect of preventing gastrointestinal mucosa atrophy is therefore improved. Moreover, a part of the digestive juice and the digested contents can easily permeate through the tubular portion, effectively preventing the dumping syndrome.

Since at least a part of the tubular portion 3 is net-shaped, strip-shaped, slit-shaped, has the shape of non-woven fabric, or a combination thereof, the effect of limiting digestion and absorption provided by the medical tool 1 can be easily adjusted by adjusting the opening area, length, or the like.

Additionally, in the adjustment described above, the tubular portion may be made of a biodegradable material to limit the period of use.

Furthermore, when the tubular portion 3 has openings like a net, gastrointestinal obstruction is easily prevented even if the tubular portion is twisted in the digestive tract.

The proportion of the area of the net-shaped part to the entire tubular portion 3 may be any suitable proportion. In one example, the proportion is 60% to 100%.

The openings of the net can be formed into any suitable shape by adjusting the attachment portion 2.

In the example shown in FIG. 1, by arranging pairs of opposing sides in parallel with the longitudinal direction of the tubular portion 3, the net can be configured so as not to expand in the longitudinal direction.

The open area percentage of the net may be any suitable percentage selected according to the target weight-loss effect, the area percentage of the net-shaped part, or the like. For example, when the area percentage is 100% (that is, when the tubular portion 3 is entirely net-shaped), the open area percentage of the net 31 is, for example, 1% to 99.9%, preferably 40% to 99%, more preferably 60% to 95%. The open area percentage within the above range can effectively prevent gastrointestinal mucosa atrophy. Moreover, the permeability of the tubular portion is increased, effectively preventing the dumping syndrome. The configuration also allows the medical tool 1 to provide a sufficient effect of limiting digestion and absorption.

The opening size of the net may be on the order of microns to millimeters, depending on the purpose. That is, the net may be an actual net or may substantially be porous membrane.

In the example shown in FIG. 1, the attachment portion 2 is formed integrally with the tubular portion 3 and may have the same shape as the tubular portion 3. Accordingly, the outer surface of the attachment portion 2 is net-shaped.

When the tubular portion 3 is strip-shaped, slit-shaped, perforated, unevenly shaped, membrane-shaped, or has the shape of non-woven fabric, for example, the attachment portion 2 may have the same shape.

As will be apparent to those skilled in the art, the attachment portion 2 may also be made of a material different from that of the tubular portion 3.

<A-2. Materials of Medical Tool>

Any suitable materials can be used for the attachment portion 2 and the tubular portion 3 of the medical tool 1. Examples of the materials include biodegradable materials and non-biodegradable materials.

The biodegradable material may be any suitable biodegradable material. Examples of the biodegradable material include biodegradable synthetic polymers, bio-based biodegradable materials, and combinations thereof. The biodegradable synthetic polymer may be any suitable biodegradable synthetic polymer. Examples of the biodegradable synthetic polymer include glycolide polymers, dioxanone polymers, lactide polymers, and combinations thereof. Preferably, the biodegradable synthetic polymer may be a glycolide polymer, a glycolide-lactide copolymer, a glycolide-trimethylene carbonate copolymer, a glycolide-dioxanone-trimethylene carbonate copolymer, a glycolide-epsilon caprolactone copolymer, a dioxanone polymer, or a combination thereof. More preferably, the biodegradable synthetic polymer may be a glycolide polymer, a glycolide-lactide copolymer, a glycolide-trimethylene carbonate copolymer, a dioxanone polymer, or a combination thereof. The bio-based biodegradable material may be any suitable bio-based biodegradable material. Examples of the bio-based biodegradable material include an animal-based biodegradable material. Preferably, the animal-based biodegradable material may be fibroin (e.g., silk constituent), animal serosa (e.g., catgut constituent), spidroin (e.g., spider silk constituent), and combinations thereof. The entire medical tool 1 may be made of a biodegradable material. The configuration described above allows at least a part of the medical tool 1 to degrade in the digestive tract lumen. This eliminates the need for extraction by invasive procedures (e.g., surgery or endoscopic surgery) after the use of the medical tool 1. Furthermore, the period in which the obesity reduction effect is exerted can be readily adjusted by selecting an appropriate biodegradable material taking into account the durability in the digestive tract lumen.

The non-biodegradable material may be any suitable non-biodegradable material. Examples of the non-biodegradable material include synthetic polymers, bio-based materials, metals, and combinations thereof. The synthetic polymer may be any suitable synthetic polymer. Examples of the synthetic polymer include olefin polymers (e.g., polyvinyl chloride, polyethylene, and polypropylene), urethane polymers (e.g., polyurethane), silicones, amide polymers (e.g., nylon (registered trademark)), ester polymers, and combinations thereof. The bio-based material may be any suitable bio-based material. The metal may be any suitable metal. Examples of the metal include iron-containing metals (e.g., stainless steel).

The material of the medical tool 1 may typically be a synthetic polymer, a metal, or a combination thereof. This configuration reliably limits the possibility of infection during use of the medical tool 1.

The medical tool 1 may contain a radiopaque substance. Examples of the medical tool 1 containing a radiopaque substance include a medical tool to which a member containing a radiopaque substance is attached, a medical tool made of a material containing a radiopaque substance, a medical tool coated with a material containing a radiopaque substance, and a medical tool enclosing a radiopaque substance. The radiopaque substance may be any suitable substance. Examples of the radiopaque substance include barium sulfate, a suitable metal material having radiopacity, and a suitable material that is used as a radiopaque marker in a medical tool (e.g., a catheter and a stent). Examples of the metal material having radiopacity include platinum, palladium, platinum-iridium alloys, and platinum-nickel alloys. Examples of the member containing a radiopaque substance include a wire and a radiopaque thread. The member is typically made of fibers containing a radiopaque substance (e.g., barium sulfate). When the medical tool 1 contains a radiopaque substance, the position and movement of the medical tool 1 in use can be easily observed by fluoroscopy.

At least a part of the medical tool 1 may be coated with any suitable material. Examples of the material include a material containing an antimicrobial material (e.g., fluorine). Examples of specific products include "Cytop" (manufactured by Asahi Glass Co., Ltd.), "Novec EGC-1720" and "Novec EGC-1700" (manufactured by 3M), "Defensa TR" (manufactured by Dainippon Ink and Chemicals), and a combination thereof. The medical tool 1 may be coated by any suitable method. Examples of the method include a method of dipping the medical tool 1 into a coating material and then drying it, and a method of injecting a coating material onto the medical tool 1. The medical tool 1 that is coated with a material containing an antimicrobial material can easily prevent the adhesion of microorganisms mixed in the digested contents and the formation of a biofilm.

<A-3. Materials of Tubular Portion 3>

Any suitable materials can be used for the tubular portion 3. For example, the materials may be the materials of the medical tool 1 described above.

The material of the tubular portion 3 may include an elastic material. Examples of the elastic material include elastomers. Examples of the elastomers include rubber, thermoplastic elastomers, and combinations thereof. When the material of the tubular portion 3 contains an elastic material, the tubular portion can easily deform in response to gastrointestinal motility. This improves the conformability of the tubular portion to the shape of the inner wall of the digestive tract, and increases the physical stimuli given to the inner wall of the digestive tract by the digested contents. This improves the effect of preventing gastrointestinal mucosal atrophy.

At least a part of the tubular portion 3 may be made of a non-woven fabric. Any suitable fibers may be used as the fiber of the non-woven fabric. Examples of the fibers include fibers derived from olefin polymers (e.g., polypropylene fibers and polyethylene fibers), fibers derived from ester polymers (e.g., polyester fibers), and combinations thereof. When at least a part of the tubular portion 3 is made of non-woven fabric, the permeability of this part is reduced, effectively protecting the corresponding section of the digestive tract.

Preferably, at least a part of the tubular portion 3 is made of fiber. The fiber may be any suitable fiber. Examples of the fiber include fibers made of the material of the medical tool 1. The fiber may be biodegradable fiber or non-biodegradable fiber. When at least a part of the tubular portion 3 is made of fiber, at least a part of the tubular portion can be easily formed in a net shape. When the fiber is biodegradable fiber (e.g., suture), after the medical tool 1 is placed in the digestive tract, the tubular portion is gradually degraded and excreted together with feces. As such, obesity can be treated without surgery to remove the placed tubular portion from the digestive tract.

The biodegradable fiber may be any suitable biodegradable fibers. Examples of the biodegradable fibers include fibers made of the biodegradable material of the medical tool 1. Specific examples of the biodegradable fibers include PDSII (registered trademark), Maxon, Dexon (registered trademark), Vicryl (registered trademark), silk thread, spider silk, catgut, Vicryl Rapide (registered trademark), Monokryl (registered trademark), and combinations thereof. Preferably, the biodegradable fibers are PDSII (registered trademark), Maxon, Dexon (registered trademark), Vicryl (registered trademark), or combinations thereof.

The non-biodegradable fiber may be any suitable non-biodegradable fibers. Examples of the non-biodegradable fibers include fibers made of the non-biodegradable material of the medical tool 1. Specific examples of the non-biodegradable fibers include polyamide fibers, polyolefin fibers, metal fibers, and combinations thereof. Examples of the polyamide fibers include nylon (registered trademark). Examples of the polyolefin fibers include polypropylene fibers. Examples of the metal fibers include stainless steel fibers.

The fibers may contain drawn fibers. When the fiber includes drawn fiber, the fiber is less likely to be stretched, allowing for easy adjustment of the direction in which the tubular portion can expand.

The average diameter D of the fiber may be any suitable diameter. In one example, the average diameter D is 100 µm to 1 mm. When a biodegradable material is used for at least a part of the fiber, the average diameter D that is within the above range facilitates the control of the period during which the medical tool 1 maintains its shape and thus provides the effect of limiting digestion and absorption. Such control can be achieved, for example, by selecting an appropriate biodegradable fiber taking into account the durability in the digestive tract lumen.

Preferably, the fibers may form the net 31. Any suitable method can be used to form the net 31. Examples of the method for forming the net 31 include methods that include a molding step, a knitting step (e.g., a stockinette stitching step), a weaving step, a bonding step, an entangling step, or a combination of these steps. The method preferably includes a molding step, a knitting step, or a weaving step. Examples of the molding include any suitable molding. Preferably, the molding is extrusion molding. When at least a part of the net 31 is made by a method including a molding step, the direction in which the tubular portion expands can be easily adjusted. When at least a part of the net 31 is formed by a method including a knitting step or a weaving step, the material of the net can be selected from a wider range of materials. Also, the strength of the net obtained by the above method is increased. The bonding step and the entangling step can be performed by any suitable treatment. Examples of the treatment include physical treatment (for example, heat treatment and mechanical treatment), and chemical treatment.

<A-4. Specific Configuration of Attachment Portion>

As described above, the present embodiment is the medical tool 1 for placement in a digestive tract lumen as shown in FIG. 1, and includes at least one tubular portion 3, which opens at two ends, and at least one attachment portion 2, which is configured to be fixed to at least a part of the tubular portion 3 and be capable of installing the medical tool 1 in the digestive tract lumen. The tubular portion 3 is configured to be placeable along at least a part of the digestive tract, have a side surface at least a part of which is capable of conforming to the shape of the inner wall of the digestive tract, and allow a part of digestive juices or digested contents to permeate. The attachment portion 2 is configured to be placeable in the stomach 6 through the oral cavity 8 and to assume an annular shape. The attachment portion 2 may have any suitable configuration and material that facilitate oral placement. For example, the materials may be the materials of the medical tool 1 described above.

Specific examples of the present embodiment are now described.

Example 1

In Example 1, the attachment member 2a of the attachment portion 2 shown in FIG. 2 is made of a shape memory alloy. The description of the tubular portion 3 is omitted.

Material: This shape memory alloy is a Ni—Ti alloy including 54-56% Ni and the remainder Ti. For example, the shape memory alloy KIOKALLOY-R (registered trademark) of Daido Steel Co., Ltd. may preferably be used. The shape memory alloy of the example is adjusted to be softened at about 5° C. to 10° C. and hardened at about 50° C. The shape memory alloy exhibits hysteresis such that the softened alloy remains soft until the temperature reaches the hardening point and the hardened alloy remains hardened until the temperature reaches the softening point. The softened attachment member 2a is deformable and can be reduced in outer diameter when compressed in the radial direction. The size can also be reduced by collapsing it. In this state, with its temperature kept lower than the hardening point, the attachment member 2a is orally inserted into the gastric cavity together with the tubular portion 3. Then, after adjusting the placement position in the digestive tract lumen, warm water or physiological saline at 55° C. to 60° C. is introduced to heat the attachment member 2a. As a result, the attachment member 2a expands and hardens to become a ring of its memorized, original annular shape. The ring-shaped attachment member 2a is placed at a predetermined position to complete the attachment. The tubular portion 3 is then guided into the intestinal tract 7.

The example configured as above has a small outer diameter in a state in which it has cooled and softened for the oral placement into the gastric cavity. When hardened with warm physiological saline of a temperature that does not affect the human body, the attachment member 2a is shaped so as not to pass through the pylorus. When the temperature later becomes less than the hardening point, the shape is maintained as long as the temperature remains above the softening point. Given that the attachment member 2a is in the gastric cavity, the temperature generally does not fall below the softening point. Even if a large amount of cold water or the like is ingested, the attachment member 2a can be easily re-hardened with warm water.

To remove the medical tool 1, a large amount of cold water may be ingested to reduce the temperature of the attachment member 2a to the softening point or less. The attachment member 2a is thus softened, deformed, and removed through the mouth.

Additionally, the softening point and the hardening point can be adjusted by adjusting the composition. When the hardening point is lowered to about 36° C. and the medical tool 1 is orally placed while giving attention to a temperature rise, the attachment member 2a hardens at body temperature even if it has softened.

Since the attachment member 2a is made of a Ni—Ti alloy, it normally does not affect the human body. In concern for allergy to Ni or the like, a Ti plating, plastic coating, or ceramic coating may preferably be applied.

Configuration: The shape may be of a ring, a coil, a spider web, a mesh, or the like.

Figure 5A:
FIG. 5A is a schematic view showing a collapsed shape of an attachment member of an example.
Figure 5B:
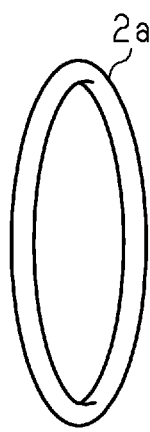
FIG. 5B is a schematic view showing a deployed shape of the attachment member of the example of FIG. 5A.

The attachment member 2a according to the embodiment of FIGS. 5A and 5B is flexible and collapsible at a predetermined temperature or lower as shown in FIG. 5A. As such, the attachment member 2a can be easily inserted through the oral cavity 8 and the esophagus 5 into the stomach 6 as shown in FIG. 3. Then, when the temperature is increased to a predetermined temperature within the stomach 6, the attachment member 2a is deployed into the memorized ring shape as shown in FIG. 5B.

Insertion Method: The attachment member 2a is sufficiently cooled to a predetermined temperature or lower (7° C. or lower) and inserted in a cooled state.

Figure 6:
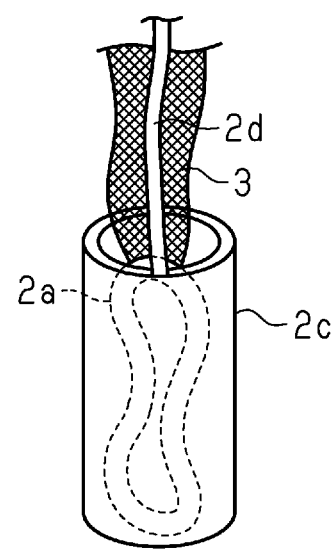
FIG. 6 is a perspective view showing a deployment prevention cover.

As shown in FIG. 6, to prevent deployment while the collapsed attachment member 2a is inserted into the stomach 6, a tubular deployment prevention cover 2c is preferably attached to prevent deployment, inserted together with the tubular portion 3 into the stomach 6, and then removed after insertion. The deployment prevention cover 2c is made of a strong material such as metal. The collapsed attachment member 2a is guided along a guide wire 2d into the deployment prevention cover 2c. During insertion, the deployment prevention cover 2c blocks the deployment of the attachment member 2a, which may be caused by an unexpected temperature rise, thereby preventing deployment in the esophagus 5. When inserted into the stomach 6, the attachment member 2a may be taken out with an endoscopic device or the like. The deployment prevention cover 2c is extracted out of the body using the guide wire 2d.

It is desirable to insert the collapsed attachment member 2a into the stomach 6 while keeping it cold with a refrigerant, a heat insulating material, or the like.

It is also desirable to prevent an unexpected deployment of the attachment member, which would otherwise be caused by a temperature rise due to the body temperature in the esophagus or the like, by using an overtube for gastric endoscopy (not shown and may be a disposable sliding tube ST-SB1S manufactured by Olympus Medical Systems Co., Ltd., for example) and quickly inserting the attachment member.

Deployment Method: The collapsed attachment member 2a inserted into the stomach is then heated and deployed by introducing warm water of a predetermined temperature, for example 50° C. to 55° C., through a tube.

Placement: First, the end of the tubular portion 3 is endoscopically inserted into the pylorus 6c. Then, the deployed attachment member 2a is endoscopically placed in the pyloric antrum 6b so that the attachment portion 2 surrounds the pylorus 6c. The tubular portion 3 does not have to be completely extended into the intestinal tract. After being pushed into the intestinal tract to some extent, the tubular portion 3 is naturally deployed into the intestinal tract 7 by the ingested food and the peristaltic movement. If necessary, it is also desirable to introduce a fluid to assist the deployment of the tubular portion 3. Furthermore, the tubular portion 3 may be endoscopically pushed into the intestinal tract.

Placement and Extraction with Foreign Body Forceps: The placement and extraction can be performed endoscopically using foreign body forceps. In this case, foreign body forceps with an outer sheath (not shown) may be used, or foreign body forceps may be used with an outer sheath. Furthermore, the overtube for gastric endoscopy described above may be used.

Placement of Tubular Portion 3 with Ileus Tube: To place the tubular portion 3, an ileus tube (not shown and may be a hydrophilic ileus tube manufactured by Create Medic Co., Ltd., for example) can be used. The ileus tube may be used to insert the tubular portion 3 into the intestinal tract 7 after the attachment member 2a is placed. The distal end of the ileus tube is fixed to the end section 3x of the tubular portion 3. For example, a guide wire is inserted into the duodenum 7a together with an endoscope, which is then pulled out. The hydrophilic ileus tube having a guide and a balloon is guided along the guide wire into the duodenum 7a. After that, the insertion proceeds under fluoroscopy. The guide functions as a weight and passes through bends by changing its position. The balloon, when filled with liquid such as water, expands narrow regions as required to assist the insertion. The insertion is continued while avoiding twisting. When the tubular portion 3 is inserted to a predetermined position, the ileus tube is pulled out. Then, with the attachment portion 2 serving as an anchor, the tubular portion 3 is extended by the peristaltic movement of the digestive tract and thus placed in the digestive tract lumen.

Removal 1: An overtube is inserted, and cold physiological saline (7° C.) is introduced to cool and plastically deform the attachment member 2a. The collapsed attachment member 2*a* is endoscopically held and pulled out. Here, the tubular portion 3 and the attachment member 2*a* may be cut in advance with scissors. The attachment member 2*a* is quickly extracted so that the collapsed attachment member 2*a* is not deployed again due to a temperature rise. In this configuration, it is also desirable to use a strong overtube capable of resisting any unexpected deployment of the attachment member 2*a*.

After removing the attachment portion 2, the tubular portion 3 is discharged out of the body by the peristaltic movement of the digestive tract.

Figure 7:
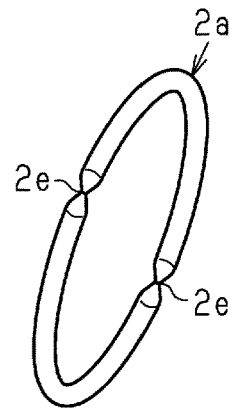
FIG. 7 is a perspective view of an attachment member having cutting sections.

Removal 2: The attachment member 2*a* may include cutting sections 2*e* that are easier to cut with scissors or heat than the other section. The cutting sections 2*e* may be formed such that they can be easily cut using an endoscope. To this end, the cutting sections 2*e* may be formed by partly reducing the diameter of the attachment member 2*a* as shown in FIG. 7 or made of a material that can be cut easily. Alternatively, a part of the attachment member 2*a* may be made of a material, such as plastic, that has a predetermined strength at body temperature but can be easily be cut using a heater and an endoscope.

Operation and Advantage (1) The attachment member 2*a*, which is made of a shape memory alloy, can be collapsed so that it easily passes through the oral cavity 8, the esophagus 5, and the cardia during oral placement.

(2) The attachment member 2*a* inserted in the stomach 6 may be heated to a predetermined shape recovery temperature with warm physiological saline so as to return to its memorized shape. The attachment member 2*a* is thus retained in the stomach 6 and does not move through the pylorus 6*c* into the intestinal tract 7.

(3) The body temperature maintains the deployed attachment member 2*a* in the deployed state. The shape memory alloy is strong and does not easily deform.

(4) Once returned to its original shape, the attachment member 2*a* is annular and thus easily surrounds the pylorus 6*c* at the pyloric antrum 6*b* in the pyloric region 6*a* of the stomach 6 and resists moving.

(5) Since the attachment member 2*a* is placed so as to surround the pylorus 6*c*, the tubular portion 3, which has one end sewn onto the attachment member 2*a*, enters the pylorus 6*c* through the inside of the annular attachment member 2*a*.

(6) When the tubular portion 3 is deployed into the intestinal tract 7, the attachment member 2*a* is pulled by the tubular portion 3 and stabilized around the pylorus 6*c*, serving as an anchor. In this manner, the inner wall of the stomach 6 is not damaged by sutures or hooks.

(7) The medical tool 1 can be removed through the mouth as needed. When cooled to a temperature less than or equal to a predetermined temperature with cold water or the like, the attachment member 2*a* loses elasticity and obtains plasticity. The attachment member 2*a* is then collapsed to be easily removed out of the body through the mouth. Additionally, the tubular portion 3 may be endoscopically separated in advance with scissors.

Example 2

Configuration: Example 2 shown in FIGS. 8A and 8B has basically the same configuration as the attachment member 2*a* of Example 1, but Example 2 is characterized in that the ring, which may be made of a material such as metal, plastic, or ceramic, has sections that are made of a shape memory alloy and serve as connecting sections. The description of the tubular portion 3 is omitted.

Figure 8A:
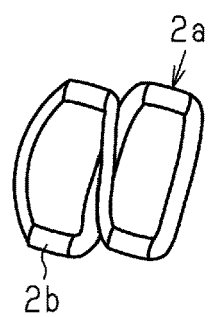
FIG. 8A is a schematic view showing a collapsed shape of an attachment member of another example.
Figure 8B:
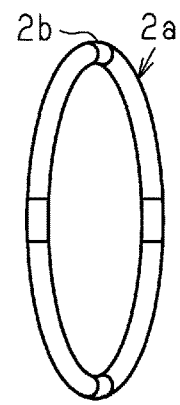
FIG. 8B is a schematic view showing a deployed shape of the attachment member of the example of FIG. 8A.

Sections of the ring-shaped attachment member 2*a* may be made of a shape memory alloy and serve as deforming sections 2*b*. As shown in FIG. 8A, a collapsed state may be achieved by collapsing at the deforming sections 2*b*.

Example 3

Configuration: The attachment portion has a mesh configuration. This method uses a metal mesh that may be used as a stent of common medical stainless steel or titanium (not a shape memory alloy). The description of the tubular portion 3 is omitted. Unlike a stent that presses against the inner wall of the intestinal tract for fixation, the deployed attachment portion 2 is fixed by being pulled by the connected tubular portion 3 toward the intestinal tract 7 and pressed around the pylorus 6*c*. The attachment portion thus functions as an anchor.

Figure 9A:
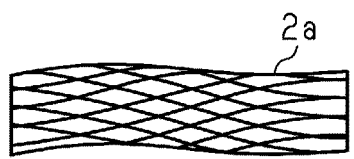
FIG. 9A is a schematic view showing a collapsed shape of an attachment member of another example.
Figure 9B:
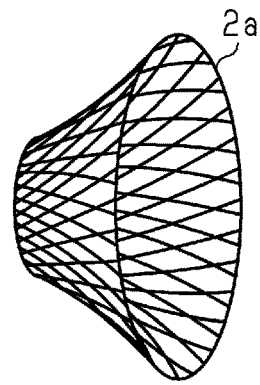
FIG. 9B is a schematic view showing a deployed shape of the attachment member of the example of FIG. 9A.

As shown in FIG. 9A, the attachment member 2*a* of this embodiment has a tubular shape when collapsed. As shown in FIG. 9B, the attachment member 2*a* is deformed into a trumpet shape or a funnel shape with a balloon in the stomach.

Figure 10:
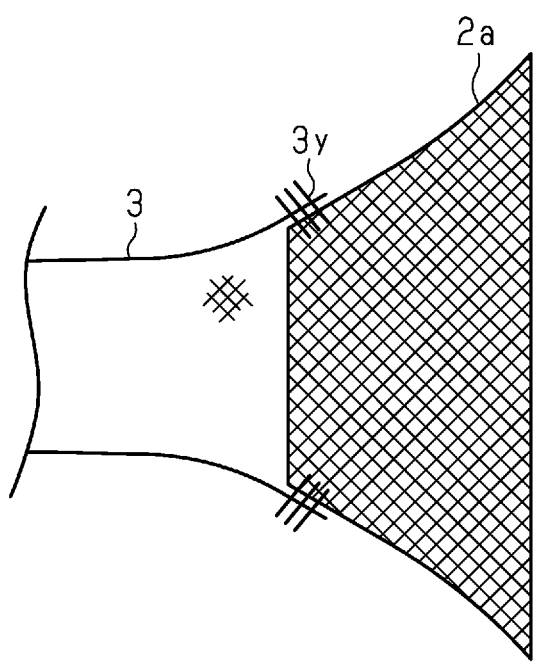
FIG. 10 is a partial cross-sectional view of an attachment portion of a medical tool according to another embodiment of the present invention.
Figure 11:
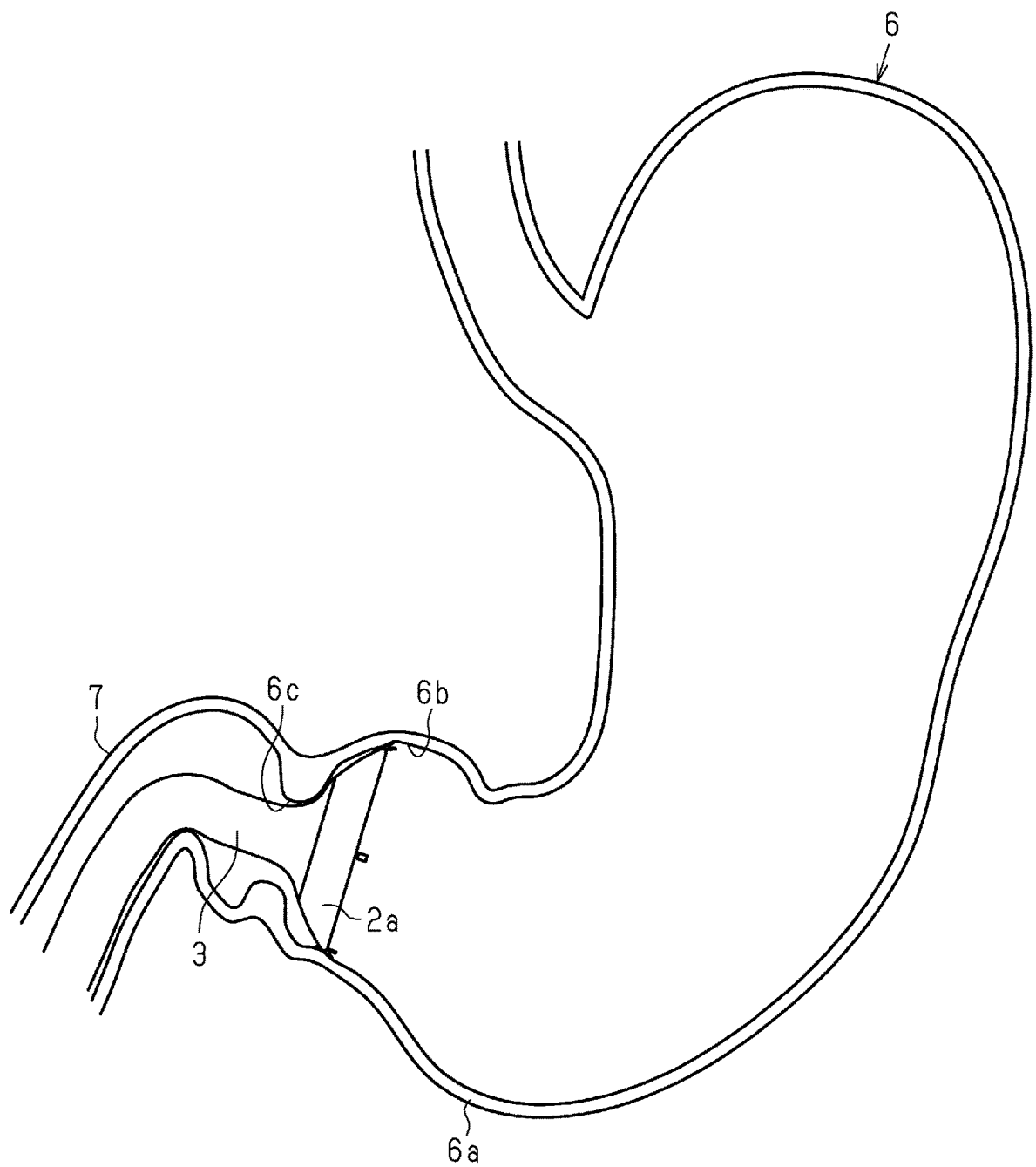
FIG. 11 is a schematic view showing the placement of the medical tool of FIG. 10 in a digestive tract.

Unlike Example 1, which is shown in FIG. 2 and fixes the attachment member 2*a* by surrounding it with the end section 3*y* of the tubular portion 3, Example 3 fixes the tubular portion 3 to an end of the attachment member 2*a* by suturing or bonding, for example, as shown in FIG. 10. The attachment member 2*a* that has deformed into a trumpet shape as shown in FIG. 11 is placed at the pyloric antrum 6*b* in the pyloric region 6*a* of the stomach so as to surround the pylorus 6*c*, and the tubular portion 3 extends from the pylorus 6*c* into the intestinal tract 7. Preferably, the position of the attachment portion 2 may also be fixed on the stomach wall 6*e* with clips 12, 14 (see FIGS. 23 and 24).

Figure 12A:
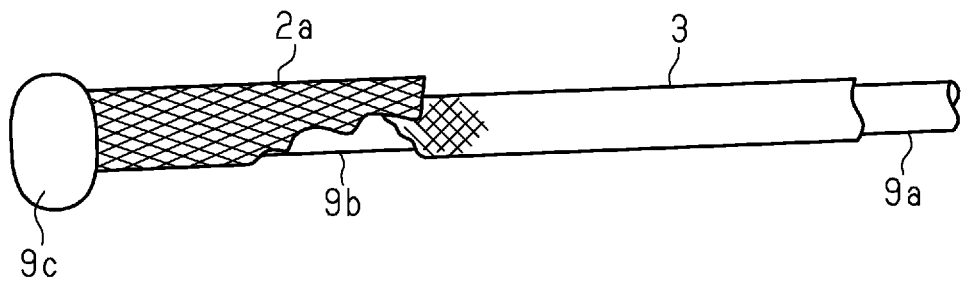
FIG. 12A is a schematic view showing the shape during insertion of an attachment member of another example.
Figure 12B:
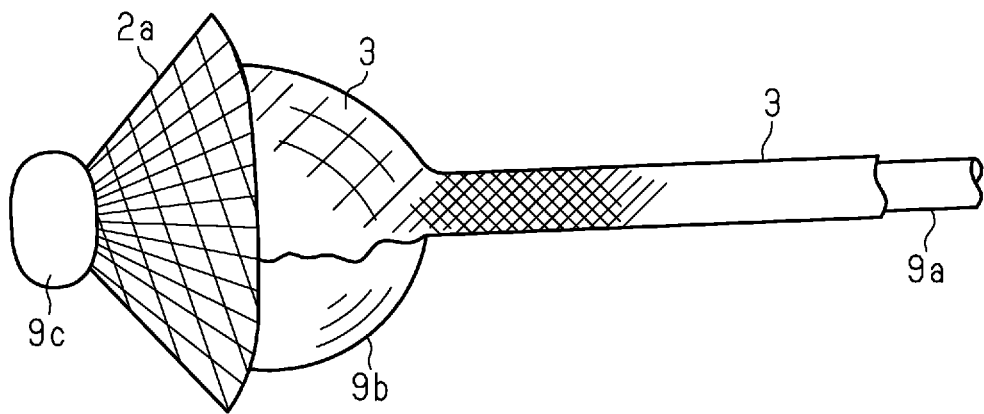
FIG. 12B is a schematic view showing a deployed shape of the attachment member of the example of FIG. 12A.
Figure 12C:
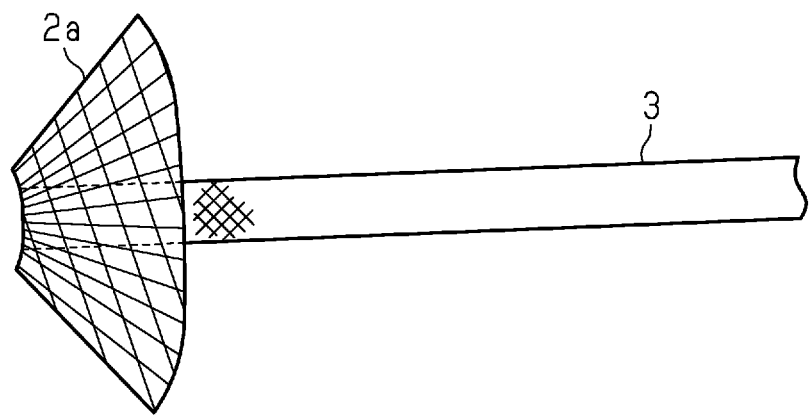
FIG. 12C is a schematic view showing the shape during the placement of the attachment member of the example of FIG. 12A.

Placement Procedure:

FIGS. 12A to 12C are schematic views showing a method for placing the attachment member 2*a* of the example. As shown in FIG. 12A, the attachment member 2*a* is in a closed tubular state, and the mesh tubular portion 3 is folded back to be placed inside the attachment member 2*a* and extends toward the oral cavity. A balloon catheter 9*a* extends through the tubular portion 3. A retaining balloon 9*c* arranged at the distal end of the balloon catheter 9*a* is filled with liquid and inflated (expanded) so that the balloon catheter 9*a* does not fall out of the attachment member 2*a*. Additionally, a dilation balloon 9*b* arranged in the attachment member 2*a* is in a deflated (contracted) state. In this state, the attachment member 2*a* is inserted into the stomach 6 through the oral cavity 8 using an overtube for gastric endoscopy. Then, the retaining balloon 9*c* is positioned to be in contact with the pylorus 6*c*.

As shown in FIG. 12B, the dilation balloon 9*b* is inflated by introducing liquid. The dilation balloon 9*b* has a length of about twice the length of the attachment member 2*a*. Upon inflation, the end of the attachment member 2*a* opposite to the pylorus 6*c* is expanded, so that the attachment member 2*a* becomes flared.

As shown in FIG. 12C, when the attachment member 2*a* is sufficiently expanded, both the retaining balloon 9*c* and the dilation balloon 9*b* are completely deflated, and then the balloon catheter 9*a* is pulled out. The tubular portion 3 is then pushed into the intestinal tract 7 from the pylorus 6*c* with an endoscopic device or the like. The attachment member 2*a* that has been formed into a flared shape is positioned to surround the pylorus 6*c*. When the tubular portion 3 is sufficiently extended and introduced into the intestinal tract 7, the attachment member 2*a* is held in close contact with the pyloric antrum 6*b* in a stable manner.

Operation and Advantage: The medical tool 1 is easily placed at a predetermined position through the mouth.

Example 4

Figure 13A:
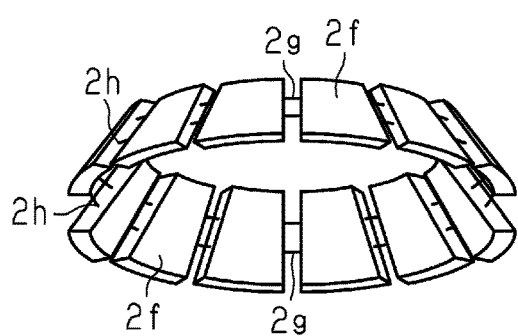
FIG. 13A is a schematic view showing a collapsed shape of an attachment member of another example.
Figure 13B:
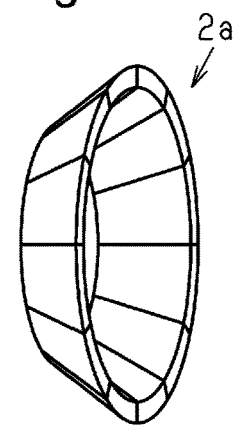
FIG. 13B is a schematic view showing a deployed shape of the attachment member of the example of FIG. 13A.

Configuration: The attachment member 2*a* includes multiple members and a string-shaped member extending through these members. The string-shaped member is tightened to integrate these members. As shown in FIG. 13A, the medical tool 1 of this example includes multiple fan-shaped pieces 2*f*, which may be made of plastic, metal, or ceramic and have holes 2*h* extending in the tangential direction. Threadlike wire-shaped members 2*g* extend through the holes 2*h* and are tightened. As shown in FIG. 13B, the attachment member 2*a* having the shape of the side surface of a truncated cone is thus formed. The description of the tubular portion 3 is omitted.

Placement Method: A collapsed state is easily achieved by loosening the wire-shaped members 2*g*. To tighten the wire-shaped member 2*g*, which has low elasticity, the wire-shaped member 2*g* may be physically pulled. Alternatively, the loosened wire-shaped member 2*g* may be contracted and tightened by means of chemical action, heat, or ultraviolet light.

Furthermore, the attachment member 2*a* may be shaped by the wire-shaped members with elasticity and contracted for insertion.

Removal: The attachment member 2*a* can be disassembled by cutting the wire-shaped members 2*g* with scissors and an endoscope.

Operation and Advantage: The attachment member 2*a* can easily deform when the wire-shaped members 2*g* are loose, allowing for the easy oral placement into the stomach.

Example 5

Configuration: A thin plate of plastic or metal, such as a shape memory alloy in particular, is formed into the shape of the side surface of a truncated cone, a funnel, or a donut-shaped disc. The description of the tubular portion 3 is omitted.

Figure 14A:
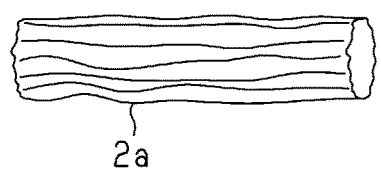
FIG. 14A is a schematic view showing a collapsed shape of an attachment member of another example.
Figure 14B:
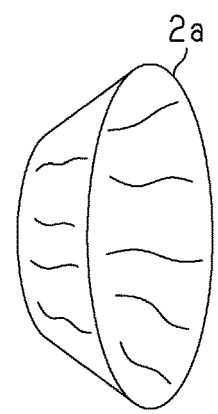
FIG. 14B is a schematic view showing a deployed shape of the attachment member of the example of FIG. 14A.

When deployed, the attachment member 2*a* may have the shape of the side surface of a truncated cone as shown in FIG. 14B. The attachment member 2*a* is collapsed into a tubular shape by forming small creases as shown in FIG. 14A. In this small shape, the attachment member 2*a* can be easily placed into the stomach through the mouth.

Figure 15A:
FIG. 15A is a schematic view showing a collapsed shape of an attachment member of another example.
Figure 15B:
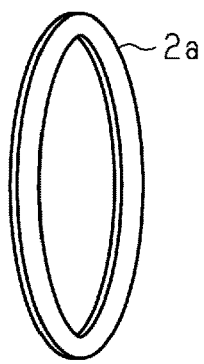
FIG. 15B is a schematic view showing a deployed shape of the attachment member of the example of FIG. 15A.

Alternatively, as shown in FIG. 15A, a thin plate of plastic or metal, such as a shape memory alloy in particular, is cut out into a donut shape and then unwound as shown in FIG. 15B.

Deployment Method: For example, the attachment member 2*a*, which may be a thin plastic plate with elasticity, is collapsed and retained with a clip or a string so as not to be deployed, and then inserted. After insertion, the clip or string is removed, so that the attachment member 2*a* is autonomously deployed and maintains its shape.

Other Examples: The attachment member 2*a* that is made of a shape memory alloy and described in Example 1 may be formed by a thin plate as in the present example.

Additionally, the attachment member 2*a* may be made of a polymeric material that swells by absorbing water.

Operation and Advantage: The attachment member 2*a* that has the shape of the side surface of a truncated cone or a funnel is placed at the pyloric antrum 6*b* in the pyloric region 6*a* of the stomach 6 in a more stable manner. Also, a disc-shaped object has a simple shape, is easy to form, and can be reduced in size by simply rolling it.

Example 6

Figure 16A:
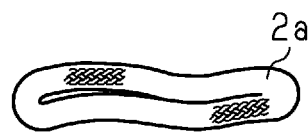
FIG. 16A is a schematic view showing a collapsed shape of an attachment member of another example.
Figure 16B:
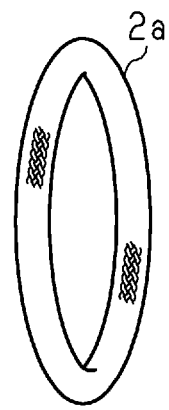
FIG. 16B is a schematic view showing a deployed shape of the attachment member of the example of FIG. 16A.

Configuration: The attachment member 2*a* is made of a flexible material and cured by a curing means when placed. For example, the attachment member 2*a* is made of a soft material such as fiber. As it is, it does not function as an anchor as shown in FIG. 16A. The attachment member 2*a* is cured in the deployed state after being placed in the stomach as shown in FIG. 16B. The description of the tubular portion 3 is omitted.

Specific Configuration:

Referring to FIG. 16B, the attachment member 2*a* includes a plastic or metal annular core, which has low elasticity, and fibers, which are knitted in a seamless annular shape. The attachment member 2*a* is flexible and porous. This attachment member 2*a* is impregnated with an ultraviolet curable resin (photopolymerization resin). The attachment member 2*a* thus configured is collapsed as shown in FIG. 16B, fixed in a collapsed state with a clip, a string, or the like, and orally inserted into the stomach 6.

When the clip or string is removed inside the stomach, the elastic force of the core member allows the attachment member 2*a* to be autonomously deployed into an annular shape. The attachment member 2*a* is then irradiated with ultraviolet light for about 20 seconds using an endoscope or the like, and the resin is thus cured by photopolymerization. As a result, the attachment member 2*a* loses its flexibility and serves more effectively as an anchor.

Examples of the ultraviolet curable resin include acrylate radical polymerization resin and epoxy cationic polymerization resin.

As the material for curing the flexible attachment member 2*a* inside the stomach 6, instead of the ultraviolet curable resin described above, a material that is cured over time in response to moisture, temperature, or pH, for example, in the stomach may be used.

Example 7

Configuration: Example 7 includes a ring-shaped elastic body made of plastic or metal. The attachment member 2*a* is collapsed before placement and deployed when placed. The description of the tubular portion 3 is omitted.

Figure 17A:
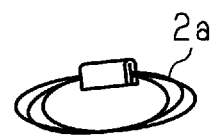
FIG. 17A is a schematic view showing a collapsed shape of an attachment member of another example.
Figure 17B:
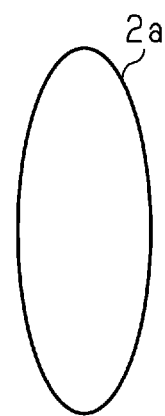
FIG. 17B is a schematic view showing a deployed shape of the attachment member of the example of FIG. 17A.

Specific Configuration: As shown in FIG. 17B, the ring-shaped elastic body made of plastic or metal is annular in a free state due to its elasticity. The elastic body is twisted twice or three times to be collapsed into a small ring of two or three turns as shown in FIG. 17A. In this state, a clip or a string is used to prevent the attachment member 2*a* from being deployed due to its elasticity. The oral insertion into the stomach 6 in the collapsed state is the same as the other examples. When the clip or string is removed inside the stomach, the attachment member 2*a* is deployed easily and autonomously by its elasticity.

Operation and Advantage: It has a simple configuration.

Example 8

Configuration: The attachment member 2*a* includes a deformable tube of bellows or a flexible pipe and is formed into an annular shape when placed. The description of the tubular portion 3 is omitted.

Figure 18A:
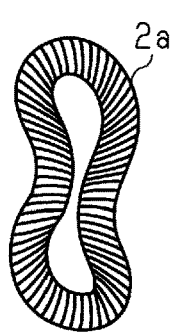
FIG. 18A is a schematic view showing a collapsed shape of an attachment member of another example.
Figure 18B:
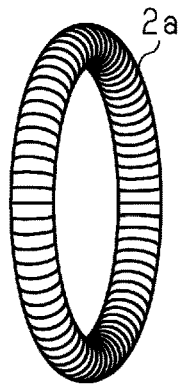
FIG. 18B is a schematic view showing a deployed shape of the attachment member of the example of FIG. 18A.

Specific Configuration: Examples of the configuration include a configuration in which a cylindrical pipe is folded into bellows to facilitate bending, a configuration in which a coil spring is covered with a flexible plastic film, a configuration in which a large number of short tubular members are combined, and a material formed by weaving a thin elastic wire-shaped member. These configurations each form an annular ring that can entirely and easily deform. Based on such a configuration, the attachment member 2a, as shown in FIG. 18B, may be formed by adding a structure that provides its elasticity and autonomously maintains an annular shape, or by enclosing an elastic body as a core member.

Attaching Method: As shown in FIG. 18A, the attachment member 2a is compressed for insertion. In this case, it may be inserted through the mouth while being compressed with a device, but it is also preferable to use a clip or a binding thread to maintain the compressed state until it is deployed in the stomach 6. Then, the attachment member 2a is attached in the same manner as in Example 1.

Example 9

Configuration: The attachment portion includes a wire-shaped member having a bendable bending section and an engageable engaging section in parts of the wire-shaped member. The attachment portion is formed into an annular shape when placed. The description of the tubular portion 3 is omitted.

Figure 19A:
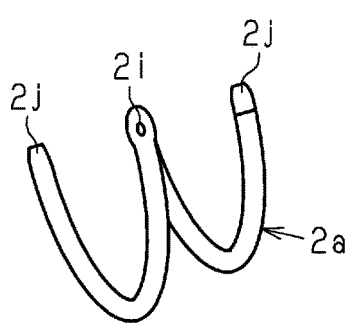
FIG. 19A is a schematic view showing a collapsed shape of an attachment member of another example.
Figure 19B:
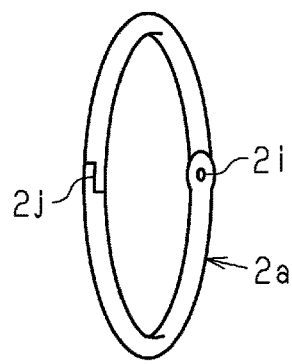
FIG. 19B is a schematic view showing a deployed shape of the attachment member of the example of FIG. 19A.
Figure 19B:
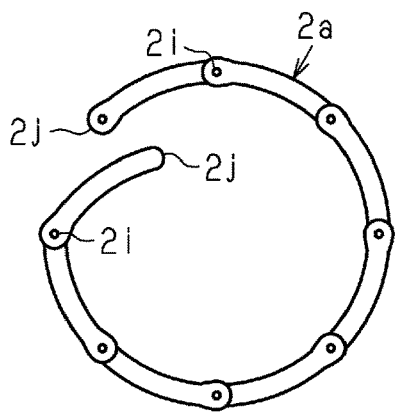

Specific Configuration:

Configuration 1: As shown in FIG. 19B, the attachment member 2a forms a rigid annular ring of plastic or metal and is divided into two parts like a card ring. Each of the divided parts includes a movable section 2i at one end and a connecting section 2j at the other end. As shown in FIG. 19A, the movable sections 2i are pivotally attached to each other to be rotatable. For example, the connecting sections 2j are step-shaped and configured to engage with each other in a removable manner by the elastic urging force of the ring.

The ring shown in FIGS. 19A and 19B are divided into two parts, but the ring may be divided into eight parts as shown in FIG. 19C. In this case, the ring has seven movable sections 2i, and each movable section 2i includes an angle-restricting means (not shown), which limits the movable range such that the movable section 2i does not open beyond the position along the arc. The connecting sections 2j/2j are provided only in one part. When the connecting sections 2j/2j are unlocked, the movable sections 2i bend inward of the arc, allowing the attachment member 2a to be collapsed into a smaller size.

When each movable section 2i is pressed outward to extend along the arc and the connecting sections 2j/2j are locked, the attachment member 2a is maintained in a circular shape.

Although not shown, the number of divided parts may be any number greater than or equal to two and may be 16 or more. Furthermore, the ring does not have to be divided at equal intervals and may be irregularly divided at uneven intervals. The specific configuration of the connecting sections 2j/2j may be modified. For example, one of the connecting sections of a pair may be fitted into the other.

Figure 20A:
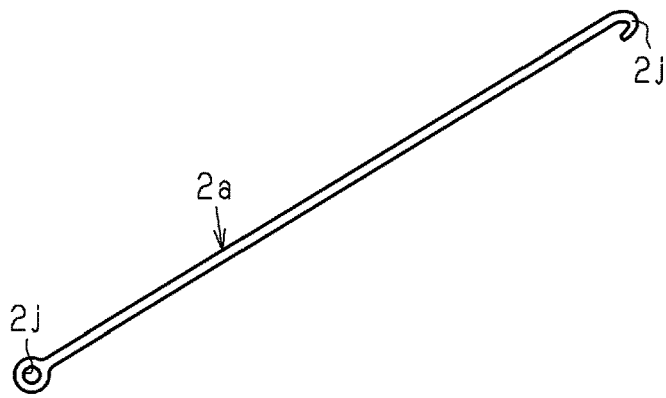
FIG. 20A is a schematic view showing a collapsed shape of an attachment member of another example.
Figure 20B:
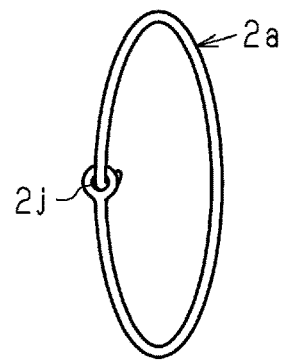
FIG. 20B is a schematic view showing a deployed shape of the attachment member of the example of FIG. 20A.

Configuration 2: As shown in FIG. 20A, the attachment member 2a may be a linear member of plastic having elasticity or metal, and connecting sections 2j are formed at its opposite ends. The connecting section 2j at one end is ring-shaped, and the connecting section 2j at the other end is hook-shaped. As shown in FIG. 20B, the attachment member 2a is curved to form an annular shape. Engaging the hook with the ring limits unintentional disengagement since the elasticity of the attachment member 2a urges the attachment member 2a in the direction that maintains the engagement.

Although the tubular portion 3 is not shown, its end section may be fixed to the attachment member 2a along a section between the connecting sections 2j/2j such that the tubular portion 3 is substantially tubular and partially opens when the connecting sections 2j/2j are locked. The tubular portion 3 does not have to have a completely closed tubular shape. A tubular shape that is cut open still provides a sufficient weight-loss effect.

Figure 21A:
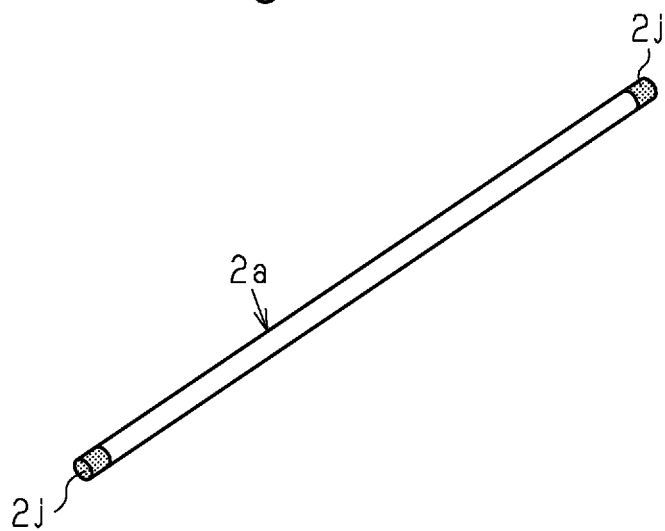
FIG. 21A is a schematic view showing a collapsed shape of an attachment member of another example.
Figure 21B:
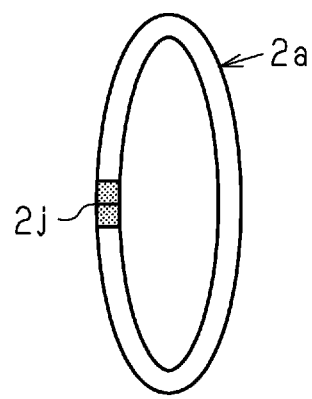
FIG. 21B is a schematic view showing a deployed shape of the attachment member of the example of FIG. 21A.

Configuration 3: As shown in FIG. 21A, the attachment member 2a may be a linear member of plastic having elasticity or metal, and connecting sections 2j are formed at its opposite ends. The connecting sections 2j are neodymium magnets, which are gold-plated to protect from gastric acid and for hygienic reasons. The magnet placed at one end differs in polarity from the magnet placed at the other end. As shown in FIG. 21B, the connecting sections 2j are attracted and strongly connected to each other to maintain the annular shape.

Operation and Advantage: Parts of the annular attachment member 2a can be separated from each other. When the attachment member 2a is inserted into the stomach 6 through the mouth, these parts are separated for easy insertion. In particular, the attachment member 2a in a linear shape is extremely easy to insert. Furthermore, the magnet connecting sections 2j attract each other, facilitating a process of connecting the connecting sections 2j together in the stomach.

Example 10

Figure 22A:
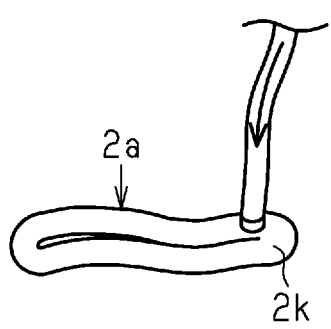
FIG. 22A is a schematic view showing a collapsed shape of an attachment member of another example.
Figure 22B:
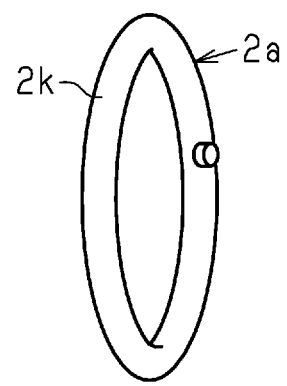
FIG. 22B is a schematic view showing a deployed shape of the attachment member of the example of FIG. 22A.

Configuration: The attachment member 2a includes a hollow donut-shaped bag 2k and a filler to be introduced in the bag 2k. Before placement, the attachment member 2a is flexible as shown in FIG. 22A. After placement in the stomach 6, the filler is introduced into the bag 2k, deploying the attachment member 2a into an annular shape as shown in FIG. 22B. The description of the tubular portion 3 is omitted.

Specific Configuration: The bag 2k having the shape of a ring buoy is filled with the filler and is thus deployed. The filler is fluid while being introduced. After introduced, the filler may lose fluidity over time or due to the body temperature. Alternatively, a filler that does not lose fluidity after being introduced (air, physiological saline, or silicone gel) may be used, and the shape may be maintained by sealing the filling port after the bag 2k is filled.

Removal: A filler that does not lose fluidity can be easily removed by breaking the bag 2k. A filler that loses its fluidity at body temperature can obtain fluidity with hot or cold water. The filler can then be easily removed by breaking the bag 2k. A filler that has lost its fluidity may be removed by using a material that dissolves the filler or by physically breaking it with scissors and an endoscope, for example. Additionally, a material that is degraded by gastric juice or the like is also desirable.

Operation and Advantage: The empty bag 2k can be collapsed and thus easily inserted into the stomach through the mouth. Also, the bag 2k can be easily removed by breaking it or by fluidizing or degrading the filler.

Example 11

Configuration: The attachment member 2a is made of a material that is degradable in the digestive tract lumen.

Specific Configuration: Although not shown, the attachment member 2a may be made of a biodegradable material, such as biodegradable synthetic polymers and bio-based biodegradable materials described above. This allows at least a part of the medical tool 1 to be degraded in the digestive tract lumen after a certain period.

Operation and Advantage: This configuration eliminates the need for invasive extraction procedures (such as surgery or endoscopic surgery) after the use of the medical tool 1.

Example 12

Configuration: The attachment member 2a is fixed to the stomach wall 6e. This fixation is achieved by a suture, a stapler, a clip, a hook, or an adhesive, for example.

Specific Configuration: In the medical tools 1 of Examples 1 to 11, the attachment portion 2 is shaped and sized such that the medical tool 1 is placed in a predetermined position without being fixed to the stomach wall 6e.

However, it is also possible to fix the attachment portion 2 to the stomach wall 6e in a stable manner by fixing the attachment member 2a to the stomach wall 6e using an endoscope. That is, unlike Examples 1 to 11, this example eliminates the need for the attachment portion 2 to be larger than the pylorus 6c and allows the attachment portion 2 to be sized to pass through the esophagus 5. As such, the medical tool 1 can be placed and fixed endoscopically in the pyloric region 6a of the stomach 6 via the oral cavity 8.

It is also desirable that such a fixing means be used also in Examples 1 to 11 until the tubular portion 3 is stably positioned in the digestive tract lumen by the peristaltic movement.

Figure 23:
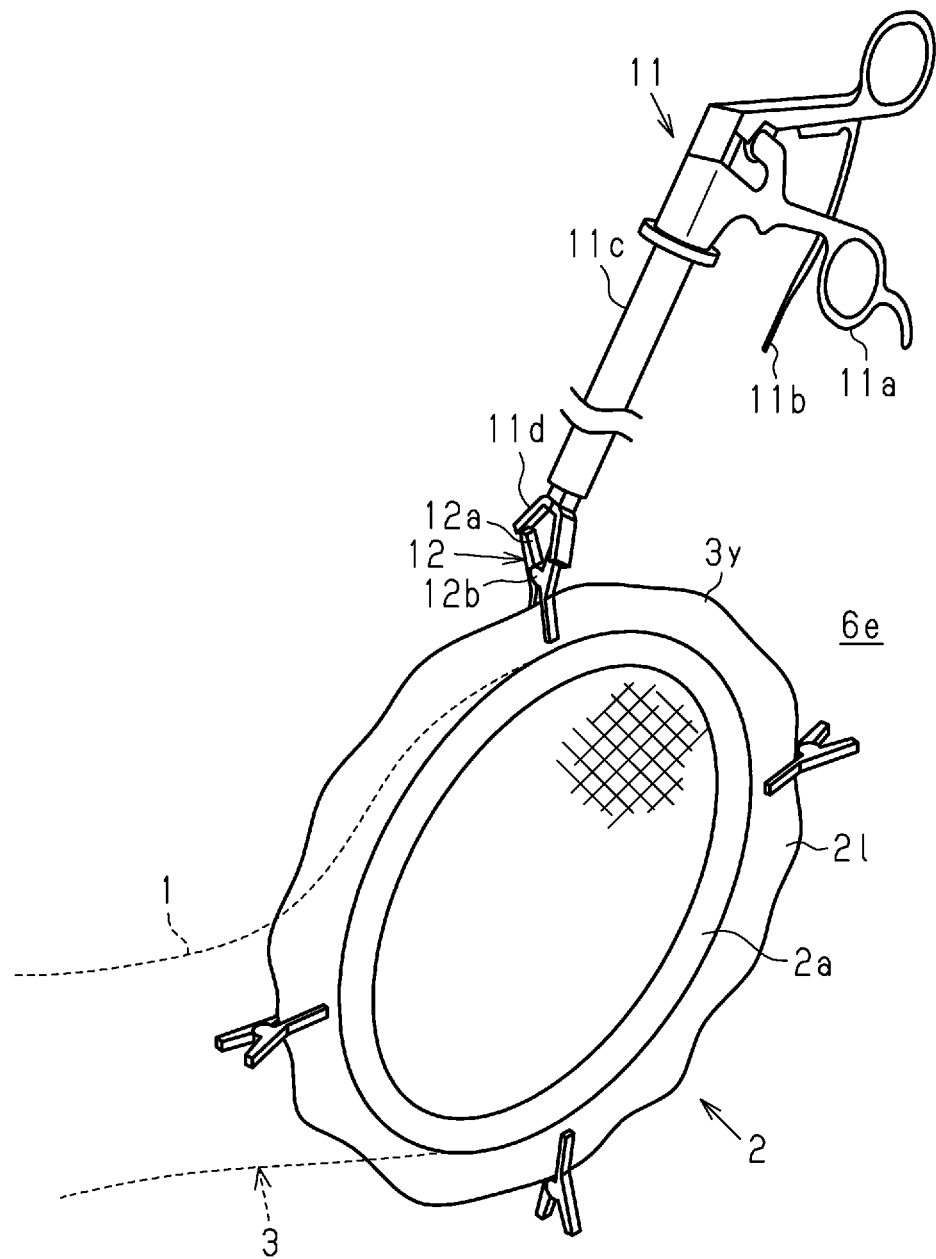
FIG. 23 is a schematic view showing an example of a fixing means for fixing an attachment member.

FIG. 23 shows an example of a fixing means for fixing the attachment portion 2. This example uses gripping forceps 11, which are an endosurgical treatment device T1101 gripping forceps Φ5 mm (serrated, with ratchet) manufactured by Olympus Medical Systems Co., Ltd., together with clips 12, which are disposable microvascular clips of TG series manufactured by Bear Medic Corporation.

The gripping forceps 11 have an insertion portion 11c, which contains a wire and is inserted into the gastric cavity through the slot of an endoscope or an overtube. A handle 11a is located outside the body. A gripping portion 11d is provided at the distal end. Opening and closing the handle 11a opens and closes the gripping portion 11d via the wire. The handle 11a has a ratchet 11b, which fixes the handle 11a in a desired position.

Each clip 12 includes a pair of members and a shaft portion 12b, which enables the members to rotate. Each member includes a pinching section 12a at the proximal end and a gripping section 12c at the distal end. A spring (now shown), which serves as an urging means, urges the gripping sections 12c in the closing direction.

As shown in FIG. 4, the attachment portion 2 of the medical tool 1 is placed at a predetermined position in the pyloric antrum 6b, and the tubular portion 3 is then extended in the direction of the duodenum 7a.

As shown in FIG. 23, with the medical tool 1 of this example, the ring-shaped attachment member 2a of the attachment portion 2 is too thick to easily hold with the clips 12. As such, the end section 3y of the tubular portion 3 is inserted into the ring-shaped attachment member 2a, folded outward to cover the ring-shaped attachment member 2a, and sewn onto the tubular portion 3. The marginal part of the end section 3y is spread outward in the shape of a flange. This flange-shaped part of the end section 3y forms a flange section 2l. When the pinching sections 12a of a clip 12 is gripped by the gripping portion 11d of the gripping forceps 11, the gripping sections 12c of the clip 12 are held in an open state. In this state, the insertion portion 11c is inserted into the cavity of the stomach 6 through the mouth. Then, the distal end of one gripping section 12c of the clip 12 catches the flange section 2l of the attachment portion 2, and the distal end of the other gripping section 12c catches the stomach wall 6e at the same time. From this state, the handle 11a is opened to open the gripping portion 11d thereby opening the pinching sections 12a of the clip 12. The gripping sections 12c thus sandwich the flange section 2l of the attachment portion 2 and the stomach wall 6e and fix them with the urging force of the spring. Further opening the handle 11a to open the gripping portion 11d separates the gripping portion 11d from the pinching sections 12a of the clip 12. After fixation, the insertion portion 11c is pulled out from the digestive tract lumen. This process is repeated to fix the flange section 2l of the attachment portion 2 to the stomach wall 6e at multiple locations, at four locations in FIG. 23, to stabilize the attachment portion 2 in the state shown in FIG. 4.

In this example, the clips 12 allow the tubular portion 3 to be stably placed within the intestinal tract after a lapse of a predetermined time, thereby stabilizing the attachment portion 2. The clips 12 may later separate from the stomach wall 6e. After the position of the attachment portion 2 is stabilized, the clips 12 may be removed again with the gripping forceps 11. The clips 12 may also be fixed to the stomach wall 6e for a long period.

Example 13

Figure 24:
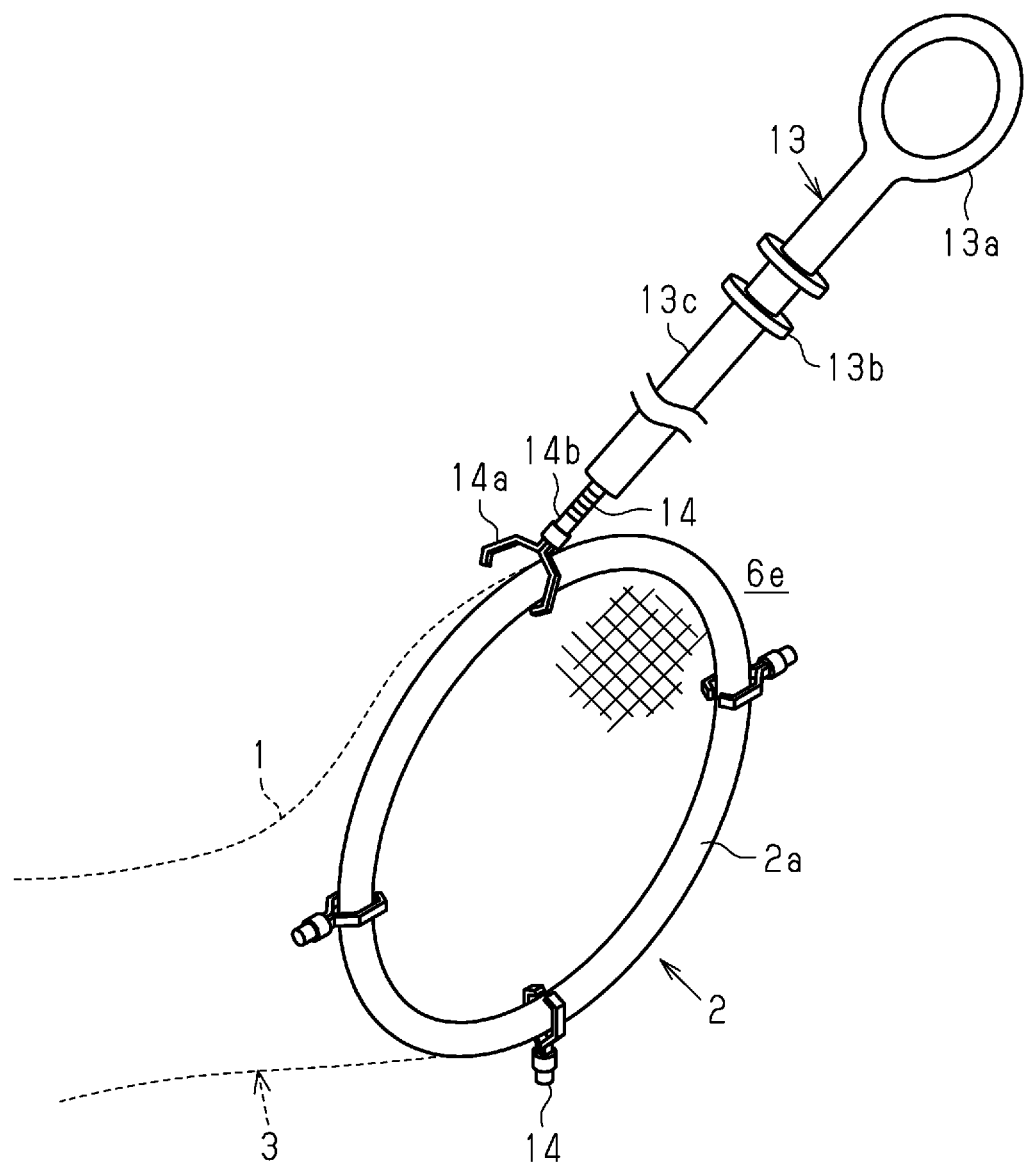
FIG. 24 is a schematic view showing another example of a fixing means for fixing an attachment member.

FIG. 24 shows an example of a fixing means for fixing the attachment portion 2. This example differs from Example 12 and uses a rotational clip device HX-110LR manufactured by Olympus Medical Systems Co., Ltd. together with long clips HX-610-090L as clips. As shown in the figure, the shape of this clip is suitable to directly catch the ring-shaped attachment member 2a of the attachment portion 2. The clip can be directly attached to the ring-shaped attachment member 2a without providing the flange section 2l as shown in FIG. 23.

The rotational clip device 13 has a sheath 13c, which contains a wire and is introduced into the gastric cavity through the slot of an endoscope. A grip 13a is located outside the body. A clip 14 is attached to the distal end. The clip 14 includes a retaining tube 14b and a pair of claws 14a inserted in the retaining tube 14b. Each claw 14a is urged by its elastic force in a direction that opens its distal end. Thus, the distal ends of the claws 14a of the clip 14 open when the claws 14a move out of the retaining tube 14b, and close when the claws 14a move into the retaining tube 14b. These movements are achieved by operating the wire in the sheath 13c with the slider 13b of the grip 13a. When the slider 13b is pulled firmly, the claws 14a are housed in the retaining tube 14b so as to be closed and locked. Pushing the slider 13b in this state detaches the clip 14. The claws 14a can be rotated by rotating the grip 13a.

The claws 14a are inserted through the slot in the endoscope in a closed state. Then, the claws 14a are opened and moved to the vicinity of the attachment portion 2, which is already placed in the gastric cavity as shown in FIG. 4. At this time, the angle of the claws 14a is adjusted to catch the ring-shaped attachment portion 2 and the stomach wall 6e together. With the ring-shaped attachment portion 2 and the stomach wall 6e caught together, the claws 14a are closed and thus locked, and the slider 13b is pressed to detach the clip 14. In this manner, the attachment portion 2 is fixed to the stomach wall 6e at multiple locations. In this example, the clips are detached from the stomach wall 6e after a certain period, but the tubular portion 3 will be stably placed in the intestinal tract by the time they are detached, allowing the attachment portion 2 to be stable. Depending on the configuration of the clips 14, the clips 14 may be fixed to the stomach wall 6e for a long period. To illustrate the state of the clips 14, FIG. 24 does not show the stomach wall 6e so that the portions hidden by the stomach wall 6e can be seen.

The fixing means is not limited to the clips, and the fixing may be achieved by a suture, a stapler, a hook, or an adhesive.

Example 14

Figure 25A:
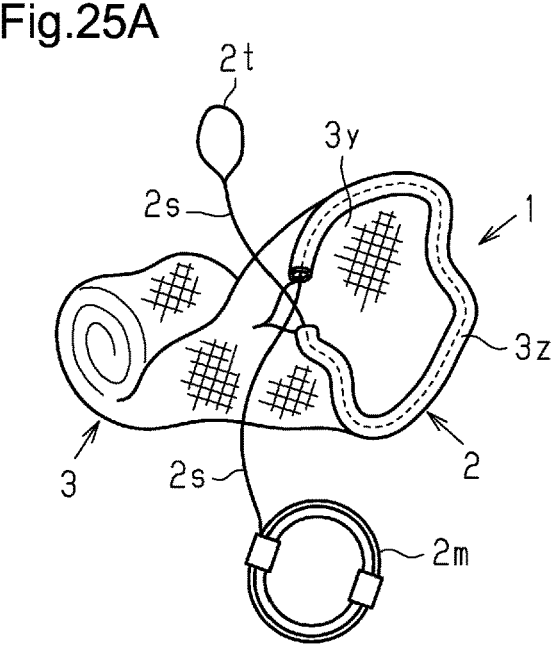
FIG. 25A is a perspective view of a tubular portion and a core member of an example in which the tubular portion is separate from the attachment member.

FIG. 25A shows the medical tool 1 in which the tubular portion 3 and a core member 2m, which serves as the attachment member 2a, are in a collapsed state. An introducing thread 2s connected to one end of the core member 2m is inserted through the end section 3y of the tubular portion 3 in advance. With the tubular portion 3 and the core member 2m collapsed into a small size, the patient swallows them through the oral cavity 8 and into the stomach 6. In the stomach 6, the core member 2m is inserted into the end section 3y of the tubular portion 3 using the introducing thread 2s. The medical tool 1 is thus assembled.

Specific Configuration: In a free state where no force is applied, the core member 2m has a linear shape as shown in FIG. 25B due to its elasticity. The connecting sections 2n of the core member 2m may be neodymium magnets, which are gold-plated or otherwise coated to protect from gastric acid and for hygienic reasons. The connecting section 2n at one end differs in polarity from the connecting section 2n at the other end. As shown in FIG. 25A, the core member 2m can be collapsed into a small shape by coiling and binding it with plastic tape, for example.

The whole tubular portion 3 is a soft mesh material and can be collapsed into a small shape. The end section 3y of the tubular portion 3 is folded back outward, and the folded part of the end section 3y is placed over the outer surface of the tubular portion 3 and fixed to form a bag shape.

As shown in FIG. 25A, the introducing thread 2s extends through the bag-shaped end section 3y of the tubular portion 3, which is collapsed into a small shape. One end of the introducing thread 2s is located at one end of the core member 2m, and the other end extends through the bag-shaped end section 3y to the outside. A ring 2t is fixed to this end of the introducing thread 2s. The ring 2t functions to prevent the introducing thread 2s from being pulled out of the bag-shaped end section 3y. The ring 2t also functions to be pulled to introduce the core member 2m into the bag-shaped end section 3y using the introducing thread 2s.

Placement Procedure: As shown in FIG. 25A, the unassembled medical tool 1 to be introduced into the stomach 6 can be swallowed by the patient through the oral cavity 8. When the plastic tape that binds the core member 2m is cut with an endoscopic device, for example, in the stomach 6, the core member 2m becomes linear as shown in FIG. 25B by its elasticity.

Figure 25C:
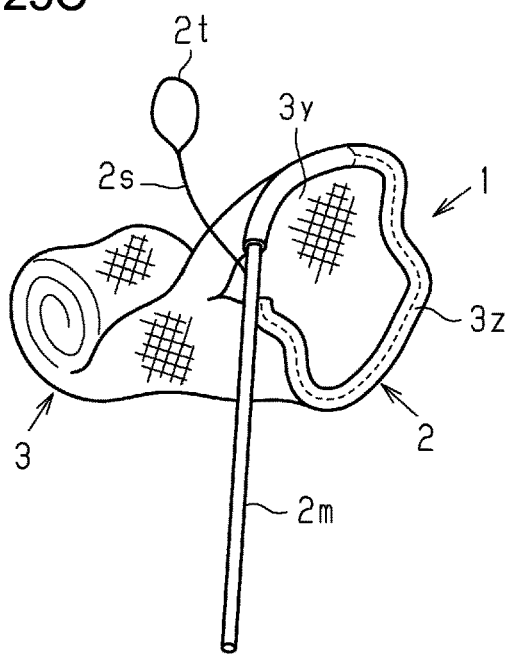
FIG. 25C is a perspective view of a state in the process of inserting the core member into the tubular portion of the example of FIG. 25A.
Figure 25B:
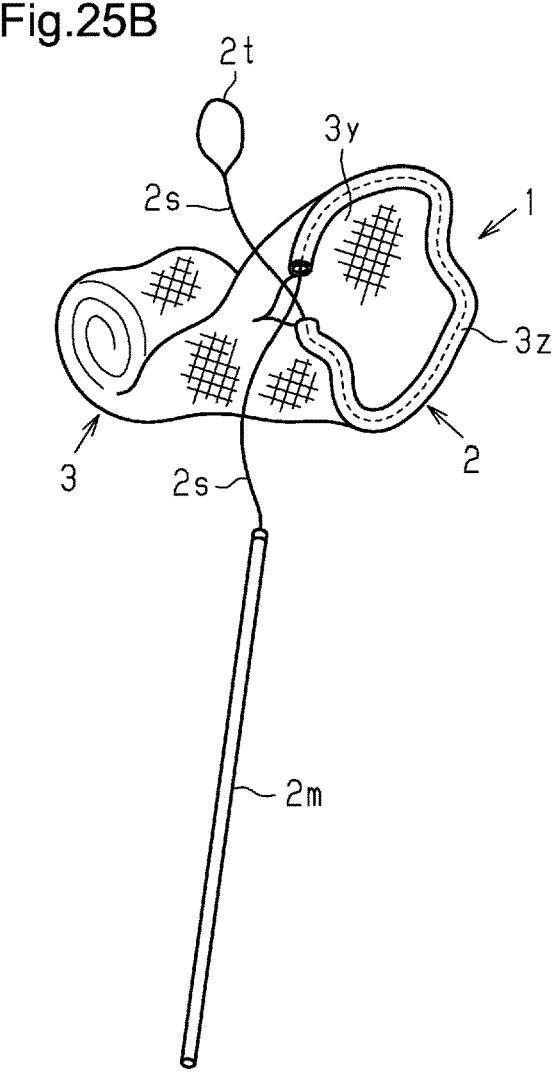
FIG. 25B is a perspective view of the core member in an extended state of the example of FIG. 25A.

Then, the ring 2t is pulled with the bag-shaped end section 3y being supported, causing the end of the core member 2m to be pulled into the bag-shaped end section 3y of the tubular portion 3 via the introducing thread 2s as shown in FIG. 25C.

Figure 25D:
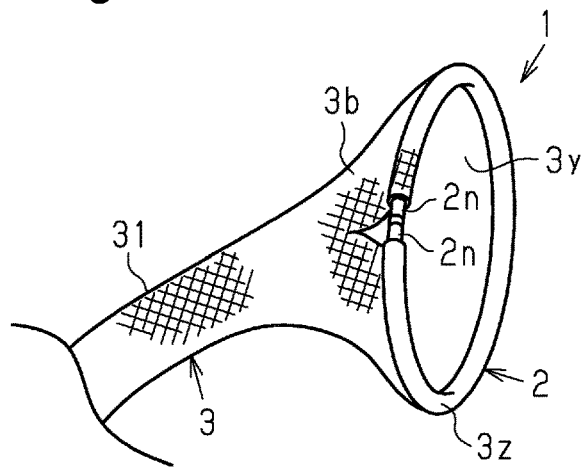
FIG. 25D is a perspective view in which the core member is attached to the tubular portion of the example of FIG. 25A.

When the distal end of the core member 2m, thus introduced in the bag-shaped end section 3y, extends out of the opening of the bag-shaped end section 3y, the introducing thread 2s at the distal end of the core member 2m is cut with scissors of an endoscopic device. In this state, the connecting sections 2n of the pair of ends of the core member 2m face toward each other. When moved closer to each other, the two connecting sections 2n are attracted and connected to each other by the magnetic force, as shown in FIG. 25D. Then, the core member 2m maintains the circular shape due to its elasticity, allowing the attachment member 2a to also maintain the circular shape.

Extraction: For extraction, the connecting sections 2n of the core member 2m are separated, and the core member 2m is pulled out of a hollow section 2l, allowing the attachment member 2a to easily deform. When the connecting sections 2n are separated, the core member 2m also returns to the linear shape due to its elasticity. As such, each member can be taken out with an endoscopic device or the like.

Operation: As described above, the attachment member 2a and the core member 2m form the fixing portion 3z (see FIG. 1) with an appropriate strength. The fixing portion 3z is sized so as not to normally pass through the pylorus 6c, allowing the medical tool 1 to be fixed at a predetermined position in the digestive tract lumen.

Advantage: The configuration allows the medical tool 1 to be more easily placed in the stomach 6 through the oral cavity. Additionally, the medical tool 1 can be easily disassembled and extracted by separating the connecting sections 2n.

Example 15

FIG. 26A shows the medical tool 1 to be placed in the digestive tract lumen. This medical tool 1 is configured to be swallowed by the patient through the oral cavity 8 into the stomach 6 with the tubular portion 3 and the core member 2m collapsed into a small shape. In the stomach 6, the attachment member 2a and the core member 2m are combined to form the fixing portion 3z. A flexible guide 2u for preshaping and guiding the core member 2m being introduced is inserted in the end section 3y of the tubular portion 3.

Specific Configuration: The attachment portion 2 of the tubular portion 3, shown in FIG. 26A, is formed by folding the end section 3y of the tubular portion 3 to enclose the annular attachment member 2a from the outside as shown in FIG. 26B. The folded end section 3y is placed over and fixed to the section of the tubular portion 3 located on the outer side to form a bag shape.

The attachment member 2a is arranged such that the guide 2u is surrounded by the end section 3y of the tubular portion 3. The guide 2u is formed by a flexible hollow tube made of a material that can deform easily, such as medical silicone rubber. As shown in FIG. 26A, the ends of the guide 2u are exposed from the end section 3y of the tubular portion 3. Accordingly, the hollow section 2l of the guide 2u is also exposed. A lubricant or the like may be applied to the hollow section 2l to reduce the coefficient of friction. The guide 2u is flexible and cannot form the fixing portion 3z by itself. The core member 2m is inserted to form the attachment member 2a, which functions as the fixing portion 3z.

The outer diameter of the core member 2m is smaller than the inner diameter of the hollow section 2l, so that the core member 2m is insertable into the hollow section 2l.

Placement Procedure: As shown in FIG. 26C, the tubular portion 3 and the core member 2m that are collapsed into a small shape can be taken orally by the patient as they are. By cutting the plastic tape with an endoscopic device, for example, the core member 2m that has been delivered into the stomach 6 through the oral cavity 8 becomes linear as shown in FIG. 26D due to the elasticity of the core member 2m. The tubular portion 3, which is flexible and does not include the core member 2m, can also be taken orally by the patient as it is. Since the guide 2u can flexibly deform, the tubular portion 3 can easily pass through the oral cavity 8 and the esophagus 5.

The linear core member 2m is inserted into one end of the hollow section 2l of the attachment member 2a such that a connecting section 2n of the core member 2m is exposed out of the other end of the hollow section 2l. A lubricant or the like may preferably be applied to the core member 2m to facilitate its insertion. As the core member 2m is inserted, the connecting sections 2n at the ends of the core member 2m are positioned to face toward each other. When moved closer to each other, the two connecting sections 2n are attracted and connected to each other by the magnetic force, as shown in FIG. 26E. Then, the core member 2m maintains the circular shape due to its elasticity, allowing the attachment member 2a to also maintain the circular shape.

Extraction: For extraction, the connecting sections 2n of the core member 2m are separated, and the core member 2m is pulled out of the hollow section 2l, allowing the attachment member 2a to easily deform. When the connecting sections 2n are separated, the core member 2m also returns to the linear shape due to its elasticity. As such, each member can be taken out with an endoscopic device or the like.

Operation: As described above, the attachment member 2a and the core member 2m form the fixing portion 3z (see FIG. 1) with an appropriate strength. The fixing portion 3z is sized so as not to normally pass through the pylorus 6c, allowing the medical tool 1 to be fixed at a predetermined position in the digestive tract lumen.

Advantage: The configuration allows the medical tool 1 to be more easily placed in the stomach 6 through the oral cavity. Additionally, the medical tool 1 can be easily disassembled and extracted by separating the connecting sections 2n.

Example 16

In the medical tool 1 shown in FIGS. 27A to 27E, the attachment member 2a is made of a shape memory alloy as in Example 1, and the tubular portion 3 and the attachment member 2a are separate members. In the same manner as Examples 14 and 15, these members are delivered into the stomach 6 through the oral cavity 8 and then combined in the stomach 6 with an endoscopic device or the like.

Figure 27A:
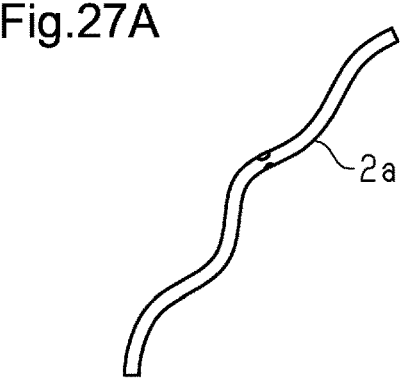
FIG. 27A is a perspective view of an attachment member of an example in which the tubular portion is separate from the attachment member.

Specific Configuration: The shape memory alloy forming the attachment member 2a is basically the same as the shape memory alloy of Example 1, and therefore the detailed description is omitted. The shape memory alloy assumes the memorized shape at the temperature in the stomach 6 and can plastically deform at higher or lower temperatures. In this example, the memorized shape is the shape of letter C, and one part of the annular shape is separated as shown in FIG. 27D. In the temperature range in which plastic deformation is possible, the attachment member 2a can be collapsed into a small shape or extended into a linear shape as shown in FIG. 27A, enabling easy passage through the oral cavity 8 and the esophagus 5.

Figure 27B:
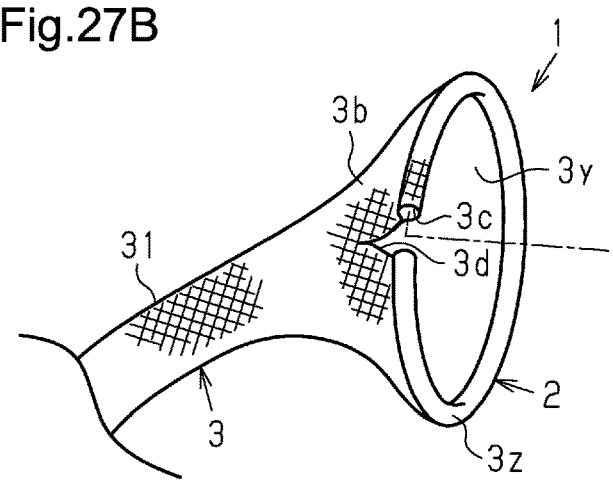
FIG. 27B is a perspective view of a tubular portion of the example of FIG. 27A.
Figure 27D:
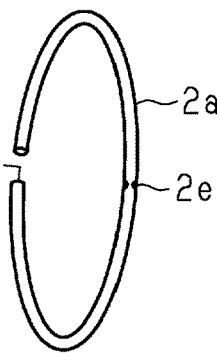
FIG. 27D is a perspective view of the attachment member of the example of FIG. 27A.
Figure 27C:
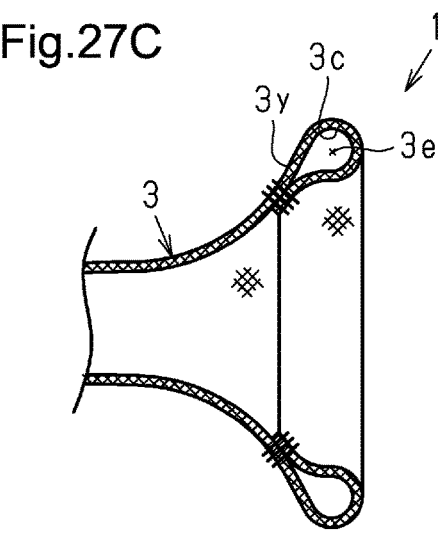
FIG. 27C is an end view of the tubular portion of the example of FIG. 27A.
Figure 27E:
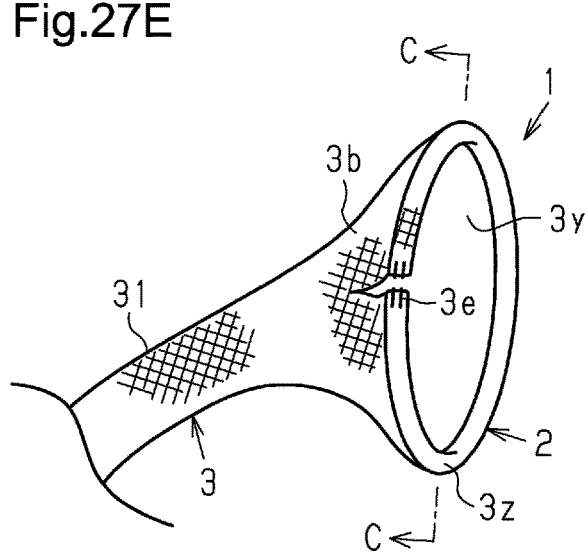
FIG. 27E is a perspective view in which the attachment member is attached to the tubular portion of the example of FIG. 27A.

As shown in FIG. 27B and FIG. 27C, which shows a cross-section taken along line C-C in FIG. 27E, the upstream end section of the tubular portion 3 is folded back to form a bag section 3c, which defines a hollow space, in the same manner as Example 14. The bag section 3c includes a cutout section 3d and has a pair of openings 3e at which the space in the bag section 3c opens. Unlike Example 14, the space in the bag section 3c does not house a tube or any other objects.

Placement Procedure: The tubular portion 3 thus configured is delivered through the oral cavity 8 into the stomach 6 with an endoscopic device or the like. Subsequently, the attachment member 2a that has been plastically deformed at a predetermined temperature is also delivered through the oral cavity 8 into the stomach 6 with an endoscopic device or the like. As shown in FIG. 27B, the attachment member 2a is inserted in the same manner as in Example 1.

One end of the attachment member 2a, which has been delivered into the stomach 6 and returned to its memorized shape of letter C due to the temperature in the stomach 6, is inserted into one opening 3e of the bag section 3c of the tubular portion 3 until the attachment member 2a is completely accommodated in the bag section 3c. Then, the openings of the bag section 3c are sewn at suture sections 3e so that the attachment member 2a is not pulled out of the bag section 3c.

Although not shown, instead of sewing, the inserted attachment member 2a may be fixed from the outside of the bag section 3c with a clip 14 as described in Example 13 and shown in FIG. 24, for example.

Extraction: In the same manner as in Example 1, the temperature of the attachment member 2a is adjusted to a temperature that enables plastic deformation, and the attachment member 2a is deformed to be endoscopically extracted. Alternatively, the attachment member 2a may be formed with a cutting section 2e of Example 1 shown in FIG. 7, and this weak section may be cut to enable endoscopic extraction.

Operation: As described above, the attachment member 2a is combined with the tubular portion 3 in the stomach 6 to form the fixing portion 3z of the medical tool 1. The fixing portion 3z is sized so as not to normally pass through the pylorus 6c, allowing the medical tool 1 to be fixed at a predetermined position in the digestive tract lumen.

Advantage: The configuration allows the medical tool 1 to be more easily placed in the stomach 6 through the oral cavity 8. Additionally, the medical tool 1 can be easily disassembled and extracted by separating the attachment member 2a from the tubular portion 3.

Example 17

FIGS. 28A to 28E show a medical tool 1 including an attachment member 2a, which is linear and elastic. The two ends of the attachment member 2a are fastened together by a wire or the like so as to be deformed into an annular shape.

Specific Configuration: Referring to FIG. 28A, the attachment member 2a of this example is made of an elastic metal or plastic. In a free state, the attachment member 2a is substantially linear.

As shown in FIG. 28B, each end of the attachment member 2a has a wire passage 2q. The wire passage 2q is a guide hole extending from the end surface of the attachment member 2a to a position of the side surface near the distal end. One extra-fine wire 15a is inserted through the pair of wire passages 2*q*. At this time, the wire 15*a* extends from the opening of the wire passage 2*q* in one end surface to the opening of the wire passage 2*q* in the other end surface. The two ends of the wire 15*a* extend from the openings of the wire passages 2*q* on the side surface at opposite ends of the attachment member and are inserted through a sheath 15*b*. The sheath 15*b* extends through the esophagus 5, and its other end is located outside the oral cavity 8 and includes a reel portion 15*d* of a wire winder 15, which is connected to the wire 15*a* through the sheath 15*b*.

For example, the two ends of the attachment member 2*a* may include magnetic connecting sections 2*n* like the attachment members 2*a* shown in FIGS. 21B and 26C, so that the two ends are attracted and attached to each other by the magnetic force.

As shown in FIGS. 28C and 28D, in another example of the two ends of the attachment member 2*a*, one end includes a plastic insertion portion 2*o*, which is injection-molded and has an elastic barb. The other end includes a fitting portion 2*p*, which receives the insertion portion 2*o* and locks the barb. The two ends can be joined with a single motion in a snap-fit manner.

Operation: When the medical tool 1 of Example 17 configured as described above is in the state shown in FIG. 28A, the wire 15*a* is wound with the wire winder 15 shown in FIG. 28E from the outside of the oral cavity 8 and through the sheath 15*b*. The wire winder 15 has a structure similar to that of a fishing reel. When the handle 15*f* is rotated in a predetermined direction, the reel portion 15*d* winds the wire 15*a*. The reel portion 15*d* rotated in the winding direction is prevented from reversing by ratchet claws 15*e*. A flange section 15*c* and the sheath 15*b* are integrally formed, and the wire 15*a* is pulled into the sheath 15*b* through the distal end placed in the stomach 6.

Consequently, as shown in FIG. 28F, the wire 15*a* bends the attachment member 2*a* such that the two ends move closer into contact with each other. At this time, in a configuration in which the two ends include the connecting sections 2*j* as shown in FIG. 21B, the connecting sections 2*j* are attracted by the magnetic force and maintain the annular shape.

In a configuration in which the insertion portion 2*o* and the fitting portion 2*p* shown in FIGS. 28C and 28D are provided, the engagement between the insertion portion 2*o* and the fitting portion 2*p* maintains the annular shape.

In either case, the wire 15*a* of the wire winder 15 is subsequently cut and removed out of the body. The attachment member 2*a* holds its annular shape without the wire 15*a*.

Advantage: The attachment member 2*a* of this example can be easily delivered into the stomach 6 in a linearly extending state with an endoscopic device or the like. The attachment member 2*a* can be formed into and maintain an annular shape in the stomach 6, thereby forming the fixing portion 3*z* of the medical tool 1 of the present invention.

Example 18

In Example 17, the attachment member 2*a* can be formed into an annular shape in the stomach 6, but the attachment member 2*a* needs to be integrally fixed with the tubular portion 3. This example illustrates a method for this fixing.

A method for fixing to the stomach wall with clips 12 is described with the medical tool 1 of Example 12 shown in FIG. 23. Additionally, a method for fixing to the stomach wall with clips 14 is described with the medical tool 1 of Example 13 shown in FIG. 24. In a similar manner, a method for fixing the attachment member 2*a* to the end of the tubular portion 3 may use the clips 12 or 14.

Operation and Advantage: In the medical tool 1 of this example, the attachment member 2*a* is formed in an annular shape separately from the tubular portion 3 and then fixed to and combined with the tubular portion 3 to form the medical tool 1.

As such, the attachment member 2*a* can be configured relatively easily.

Other Examples: The attachment member 2*a* is not limited to the one shown in Example 17, and the method is applicable to the attachment members 2*a* described in Example 1 shown in FIGS. 5A, 5B, and 7, Example 2 shown in FIGS. 8A and 8B, Example 3 shown in FIGS. 9A, 9B, 12A, 12B, 12C, 13A, and 13B, Example 5 shown in FIGS. 14A, 14B, 15A, and 15B, Example 6 shown in FIGS. 16A and 16B, Example 7 shown in FIGS. 17A and 17B, Example 8 shown in FIGS. 18A and 18B, Example 9 shown in FIGS. 19A, 19B, 19C, 20A, 20B, 21A, and 21B, and Example 10 shown in FIGS. 22A and 22B, for example. Furthermore, the attachment member 2*a* is not limited to these.

Example 19

Figure 29A:
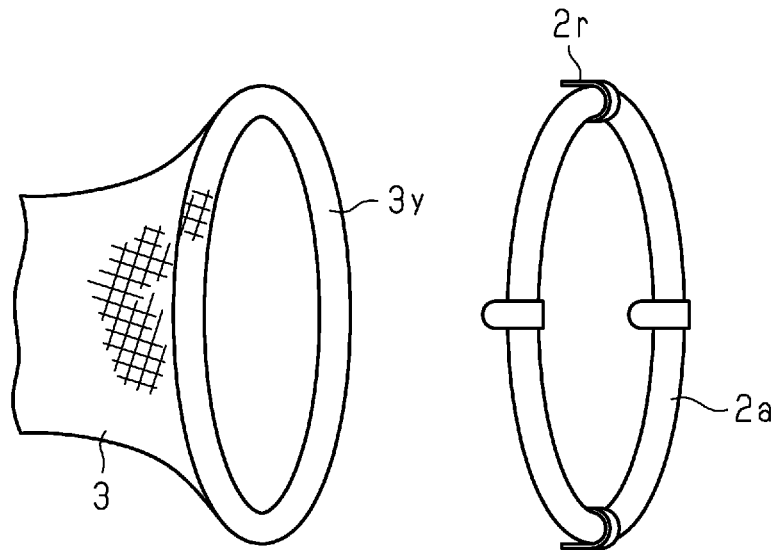
FIG. 29A is a perspective view of an example in which the tubular portion is separate from the attachment member, showing a state before the tubular portion is combined with the attachment member.
Figure 29B:
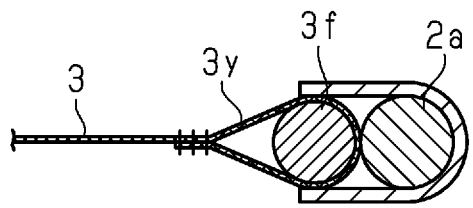
FIG. 29B is a cross-sectional view of the example of FIG. 29A showing a state after the tubular portion is combined with the attachment member.
Figure 29C:
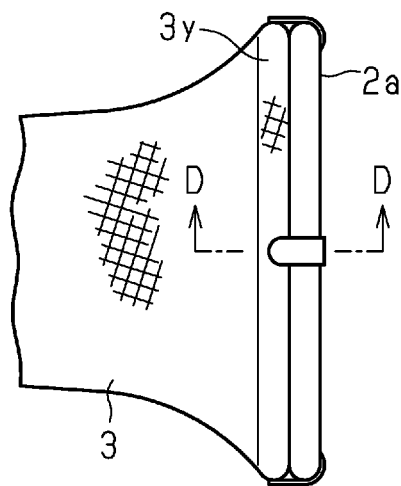
FIG. 29C is a perspective view of the example of FIG. 29A showing a state after the tubular portion is combined with the attachment member.

As shown in FIG. 29A, the attachment member 2*a* shown in FIG. 28A may be provided with fixing claws 2*r*.

Specific Configuration: The claws 2*r* are configured as pairs of opposing projections. For example, the claws 2*r* may be provided at eight positions at equal intervals. This facilitates the attachment of the attachment member 2*a* with the claws 2*r* to the end section 2*y* of the tubular portion 3 when the attachment member 2*a* is flexible, can pass through the oral cavity 8 and the esophagus 5, and assumes an annular shape in the stomach 6 due to its elasticity, like the attachment member 2*a* of Example 15 shown in FIG. 26A.

Operation and Advantage: The end section 3*y* of the tubular portion 3 is endoscopically sandwiched between the claws 2*r* with pliers or the like to fix the tubular portion 3. As compared to Example 18, the positions of the claws 2*r* are fixed since they are provided on the attachment member 2*a*, and the claws 2*r* are stable since one end is fixed. As such, inserting the end section 3*y* of the tubular portion 3 between the claws 3*r* with an endoscopic device or the like attaches the attachment member 2*a* at equal intervals. Moreover, unlike clips 12 and 14, the claws 2*r* will not fall off.

Example 20

In the medical tool 1 of yet another aspect, the attachment member 2*a* shown in Example 17 is formed separately from the tubular portion 3. The attachment member 2*a* is formed in an annular shape and then combined using fixing bands 3*g* provided on the tubular portion 3.

Specific Configuration: As shown in FIG. 29A, the attachment member 2*a* shown in FIG. 28A remains annular, and multiple strip-shaped fixing bands 3*g* extend from the end section 3*y* of the tubular portion 3. The fixing bands 3*g* may be strip-shaped portions extending from eight positions of the end section 3*y* at equal intervals and may be made of the same material as the tubular portion 3. For example, the fixing bands 3*g* may use hook-and-loop fasteners for retaining.

Figure 30A:
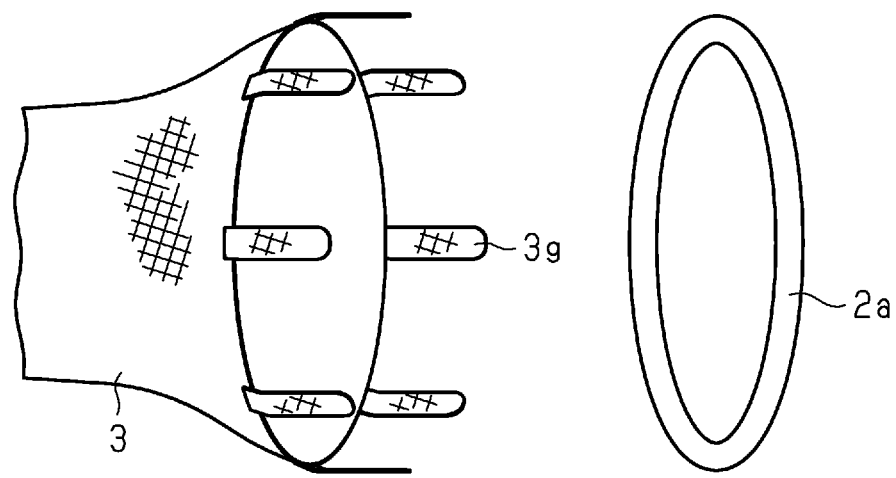
FIG. 30A is a perspective view of an example in which the tubular portion is separate from the attachment member showing a state before the tubular portion is combined with the attachment member.
Figure 30B:
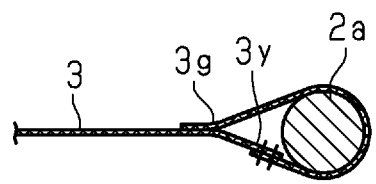
FIG. 30B is a cross-sectional view of the example of FIG. 30A showing a state after the tubular portion is combined with the attachment member.
Figure 30C:
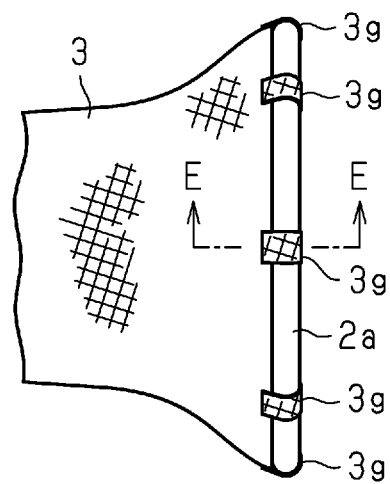
FIG. 30C is a perspective view of the example of FIG. 30A showing a state after the tubular portion is combined with the attachment member.

Operation and Advantage:

FIG. 30B shows a cross-section taken along line D-D in FIG. 30C. As illustrated, each fixing band 3*g* wraps the attachment member 2*a* from the inner side, and the hookand-loop fastener at the distal end adheres to the end section 3*y* of the tubular portion 3 from the outside.

As shown in FIG. 30C, the end section 3*y* of the tubular portion 3 is fixed along the annular attachment member 2*a*.

The hook-and-loop fastener allows for easy fixing using an endoscopic device. The fixing bands 3*g* may also be sutured.

For extraction, the attachment member 2*a* and the tubular portion 3 can be separated by cutting the fixing band 3*g* with scissors.

Example 21

Figure 31A:
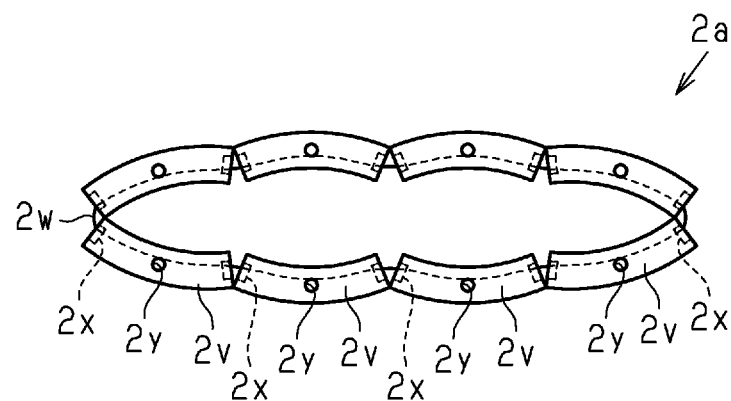
FIG. 31A is a schematic view showing a collapsed shape of an attachment member of another example.
Figure 31B:
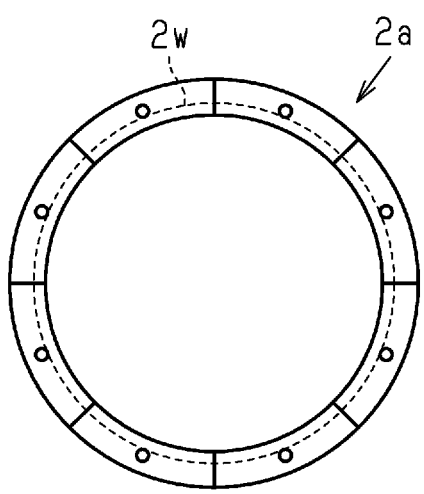
FIG. 31B is a schematic view showing a deployed shape of the attachment member of the example of FIG. 31A.

In yet another aspect, the attachment member 2*a* is deployed from the collapsed state shown in FIG. 31A into the annular shape shown in FIG. 31B. The tubular portion 3 is not shown.
Specific Configuration:

As shown in FIG. 31A, the attachment member 2*a* is formed by coupling eight pieces 2*v* into an annular shape with a connecting thread 2*w*. Each piece 2*v* is a hollow, macaroni-shaped member. The piece 2*v* has the shape of an arc with a central angle of 45° and is made of a medical metal or a hard plastic. One connecting thread 2*w* extends through the eight pieces 2*v* to form the shape of one ring. The connecting thread may be made of an elastic medical material such as a polyamide fiber or an elastomer, for example.

Each of the eight pieces 2*v* includes connecting sections 2*x* with magnets at opposite ends. The connecting sections 2*x* may have the same configuration as the connecting sections 2*j* of Example 9 shown in FIG. 21B. The magnets of the connecting sections 2*x* at the ends of adjacent pieces 2*v* of the eight pieces 2*v*, which are formed in a ring shape by the connecting thread 2*w*, are arranged such that they have opposite polarities and are attracted to one another by the magnetic force. As such, when the ends of the eight pieces 2*v* are brought into contact with each other, the attraction between these ends fixes the pieces 2*v* in the shape of a perfect circle as a whole as shown in FIG. 31C. The attachment member 2*a* thus maintains the state shown in FIG. 31C.

Each piece 2*v* has a connecting hole 2*y*, through which a thread connected to the end section 3*y* of the tubular portion 3 may be inserted to connect to the tubular portion 3.
Placement Procedure:

A thread connected to the end section 3*y* of the tubular portion 3 is inserted in the connecting hole 2*y* of each piece 2*v* to connect it to the tubular portion 3. When the attachment member 2*a* is compressed in the radial direction from this state, the attachment member 2*a* is collapsed into the state shown in FIG. 31A. The attachment member 2*a* is bound with a thread or a sheet in this state. The patient can swallow the attachment member 2*a* and the tubular portion 3 in this state through the oral cavity 8.

After the medical tool 1 is delivered into the stomach 6, the thread or sheet that binds the attachment member 2*a* is cut with an endoscopic device or the like. This allows the connecting sections 2*x* to be fixed to one another by the magnetic force to form an annular shape as shown in FIG. 31B. Then, the tubular portion 3 is deployed into the duodenum 7*a*.
Advantage:

This configuration allows the medical tool 1 to be more easily placed and deployed in the stomach 6 through the oral cavity 8. Also, the medical tool 1 can be easily disassembled and extracted by detaching the attachment member 2*a* from the tubular portion 3 and cutting the connecting thread 2*w* to separate the connecting sections 2*x* using scissors, for example.
Modifications In the present invention, the "attachment portion" is illustrated in the examples as the "attachment member 2*a*" of the "attachment portion 2", but the "attachment portion" includes a wide range of aspects that are configured to be capable of attaching the tubular portion 3 in the digestive tract lumen irrespective of the names, such as those integral with the tubular portion 3, those independent of the tubular portion 3, and those formed by multiple components.

The medical tool 1 may be delivered into the stomach 6 through the oral cavity 8 with an endoscope or the like, or may be swallowed by the patient to be delivered through the oral cavity 8. However, the present disclosure does not exclude a situation in which the medical tool 1 is placed during laparotomy or a situation in which surgery is performed for the purpose of the placement itself.

The above-described examples can be implemented by adding, deleting, and changing the configurations without departing from the scope of the claims by those skilled in the art. The above examples are intended as illustrations, and it will be apparent to those skilled in the art that the configurations illustrated in the examples, such as the configurations of the attachment member 2*a* and the tubular portion 3 and the joining methods, are interchangeable.

REFERENCE SIGNS LIST

1 . . . Medical Tool; 2 . . . Attachment Portion; 2*a* . . . Attachment Member; 2*b* . . . Deforming Section; 2*c* . . . Deployment Prevention Cover; 2*d* . . . Guide Wire; 2*e* . . . Cutting Section; 2*f* . . . Piece; 2*g* . . . Wire-shaped Member; 2*h* . . . Through-Hole; 2*i* . . . Movable Section; 2*j* . . . Connecting Section; 2*k* . . . Bag; 2*l* . . . Flange; 2*m* . . . Core member; 2*n* . . . Connecting Section (Magnet); 2*o* . . . Insertion Portion; 2*p* . . . Fitting Portion; 2*q* . . . Wire Passage; 2*r* . . . Fixing Claw; 2*s* . . . Introducing Thread; 2*t* . . . Ring; 2*u* . . . Guide; 2*v* . . . Piece; 2*w* . . . Connecting Thread; 2*x* . . . Connecting Section (Magnet); 2*y* . . . Connecting Hole; 3 . . . Tubular Portion; 3*a* . . . Uniform Region; 3*b* . . . Increasing Region; 3*c* . . . Bag Section; 3*d* . . . Cutout Section; 3*e* . . . Opening; 3*f* . . . Core member; 3*g* . . . Fixing Band; 3*x* . . . End Section; 3*y* . . . End Section; 3*z* . . . Fixing Portion; 5 . . . Esophagus; 6 . . . Stomach; 6*a* . . . Pyloric Region; 6*b* . . . Pyloric Antrum; 6*c* . . . Pylorus; 6*d* . . . Cardia; 6*e* . . . Stomach Wall; 7 . . . Intestinal Tract; 7*a* . . . Duodenum; 7*b* . . . Jejunum; 8 . . . Oral Cavity; 9*a* . . . Balloon Catheter; 9*b* . . . Dilation Balloon; 9*c* . . . Retaining Balloon; 11 . . . Gripping Forceps; 11*a* . . . Handle; 11*b* . . . Ratchet; 11*c* . . . Insertion Portion; 11*d* . . . Gripping Portion; 12 . . . Clip; 12*a* . . . Pinching Section; 12*b* . . . Shaft Portion; 12*c* . . . Gripping Section; 13 . . . Rotational Clip Device; 13*a* . . . Grip; 13*b* . . . Slider; 13*c* . . . Sheath; 14 . . . Clip; 14*a* . . . Claw; 14*b* . . . Retaining Tube

The invention claimed is:

1. An apparatus comprising:
  a medical tool configured for placement in a digestive tract lumen; and
  a balloon catheter configured to be used for the medical tool, the medical tool comprising:

at least one tubular portion opening at two ends; and at least one attachment portion configured to be fixed to at least a part of the tubular portion and be capable of installing the tubular portion in the digestive tract lumen, wherein the tubular portion is configured to:

be placeable along at least a part of a digestive tract;

include a side surface, at least a part of which is capable of conforming to a shape of an inner wall of the digestive tract; and allow a part of digestive juice or digested contents to permeate, the attachment portion is made of a metal mesh and configured to be placeable in a stomach through a mouth, the attachment portion has a tubular shape when collapsed and is configured to be deformed into a trumpet shape or a funnel shape so as to be pressed around the pylorus when deployed, the balloon catheter includes:

a retaining balloon configured to be disposed outside the attachment portion to engage a first end of the attachment portion; and a dilation balloon configured to be disposed inside the attachment portion, the retaining balloon is configured to be inflated so that the attachment portion does not fall out of the balloon catheter, and the dilation balloon is configured to be inflated to push and expand a second end of the attachment portion, thereby deforming the attachment portion into the trumpet shape or the funnel shape.

2. The apparatus according to claim 1, wherein the attachment portion is configured to be placed in a pyloric region of the stomach.

3. The apparatus according to claim 2, wherein the attachment portion is configured to be sized so as not to pass through a pylorus after the placement.

4. The apparatus according to claim 1, wherein the attachment portion comprises a medical metal.

* * * * *